US006752753B1

(12) United States Patent
Hoskins et al.

(10) Patent No.: US 6,752,753 B1
(45) Date of Patent: Jun. 22, 2004

(54) BRACHYTHERAPY INSTRUMENT AND METHODS

(75) Inventors: Matthew W. Hoskins, Bend, OR (US); Linyee Chang, Bend, OR (US); Huiwen Kong, Orangeburg, NY (US); Melissa Buan Hammerman, Bend, OR (US)

(73) Assignee: DesChutes Medical Products, Inc., Bend, OR (US)

( * ) Notice: Subject to any disclaimer, the term of this patent is extended or adjusted under 35 U.S.C. 154(b) by 257 days.

(21) Appl. No.: 10/110,562

(22) PCT Filed: Oct. 16, 2000

(86) PCT No.: PCT/US00/28668

§ 371 (c)(1),
(2), (4) Date: Apr. 12, 2002

(87) PCT Pub. No.: WO01/28631

PCT Pub. Date: Apr. 26, 2001

Related U.S. Application Data

(60) Provisional application No. 60/200,596, filed on Apr. 28, 2000, and provisional application No. 60/159,765, filed on Oct. 15, 1999.

(51) Int. Cl.[7] ............................................... A61N 5/00
(52) U.S. Cl. ......................................................... 600/7
(58) Field of Search ....................................... 600/1–8

(56) References Cited

U.S. PATENT DOCUMENTS

| 2,269,963 | A | 1/1942 | Wappler |
| 3,921,632 | A | 11/1975 | Bardani |
| 4,086,914 | A | 5/1978 | Moore |
| 4,167,179 | A | 9/1979 | Kirsch |
| 4,402,308 | A | 9/1983 | Scott |
| 4,427,005 | A | 1/1984 | Tener |
| 4,461,280 | A | 7/1984 | Baumgartner |
| 4,580,561 | A | 4/1986 | Williamson |
| 4,642,096 | A | 2/1987 | Katz |
| 4,700,692 | A | 10/1987 | Baumgartner |
| 5,053,042 | A | 10/1991 | Bidwell |
| 5,242,373 | A | 9/1993 | Scott et al. |
| 5,620,479 | A | 4/1997 | Diederich |
| 5,860,909 | A | 1/1999 | Mick et al. |
| 5,871,448 | A | 2/1999 | Ellard |
| 5,938,583 | A | 8/1999 | Grimm |
| 5,957,935 | A | 9/1999 | Brown et al. |
| 6,036,632 | A | 3/2000 | Whitmore, III et al. |
| 6,102,844 | A | 8/2000 | Ravins et al. |

FOREIGN PATENT DOCUMENTS

| WO | WO 98/56295 | 12/1998 |
| WO | WO 99/61104 | 12/1999 |

OTHER PUBLICATIONS

Nag, et al., "ABS Survey: Prostate Brachytherapy," *American Brachytherapy Society* (2000).

"Mick (R) 200–TPV Applicator," http://www.neoforma.com/pd/index.html?PageMode=Offerings&prodKey=6, 2 pages (Jun. 25, 1999).

"Ultrasonically guided transperineal seed implantation of the prostate: modification of the technique and qualitative assessment of implants," http://www.ncbi.nlm.nih.gov, 1 page (Jun. 25, 1999).

(List continued on next page.)

*Primary Examiner*—John P. Lacyk
(74) *Attorney, Agent, or Firm*—Klarquist Sparkman, LLP

(57) ABSTRACT

A brachytherapy instrument and method is disclosed for delivering therapeutic substances such as radioactive seeds, to internal organs, such as the prostate. The instrument includes a needle (602) and stylet (604) which are capable of reciprocating relative to one another, but which can be selectively fixed against such movement. The needle (602) is loaded with radioactive seeds, and the stylet (604) advances the seeds to the distal end of the needle.

91 Claims, 20 Drawing Sheets

OTHER PUBLICATIONS

"A new device for interstitial 125Iodine seed implantation," http://www.ncbi.nlm.nih.gov, 1 page (Jun. 25, 1999).

"A survey of current clinical practice of permanent prostate brachytherapy in the United States," http://www.ncbi.nlm.nih.gov, 1 page (Jun. 25, 1999).

"The Precision Stepper Kit® On–line Order Form," http://www2.digimktg.com/spp/TEqSTP110.html, 2 pages (Jun. 25, 1999).

"Prostate Brachytherapy Equipment On–Line Order Form," http://www2.digimktg.com/spp/TEquipment.html, 1 page (Jun. 25, 1999).

"Ultrasound System and Guidance Kit for Prostate Brachytherapy," http://www.siemens-ultrasound.com/prod/packages/brachy.html, 2 pages (Jun. 25, 1999).

"Brachytherapy Stepping & Stabilizing System for Seed Implantation," http://www.amertekmed.com/index2.htm, 2 pages (Jun. 25, 1999).

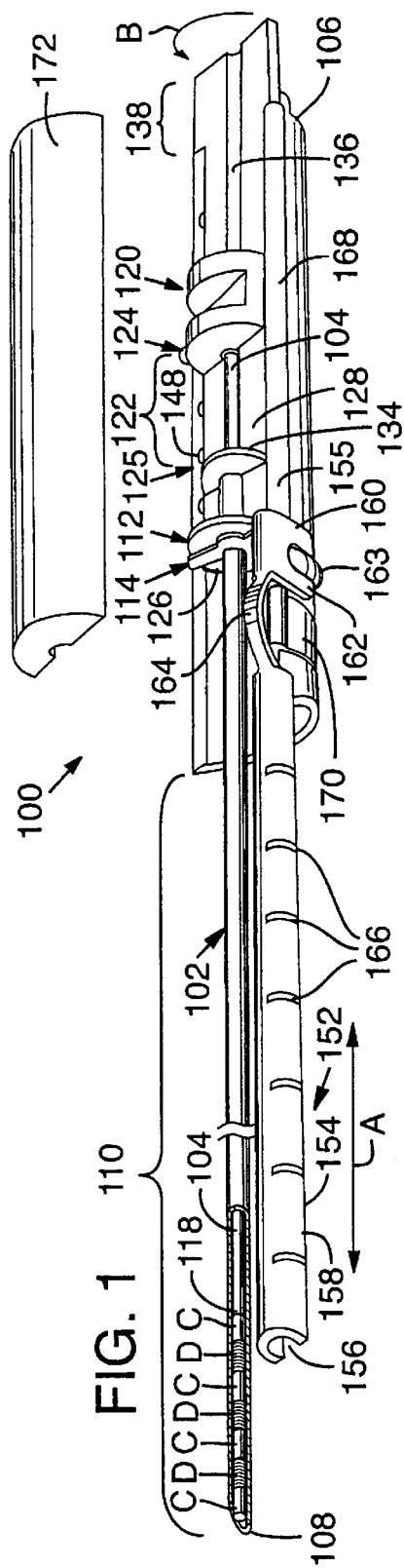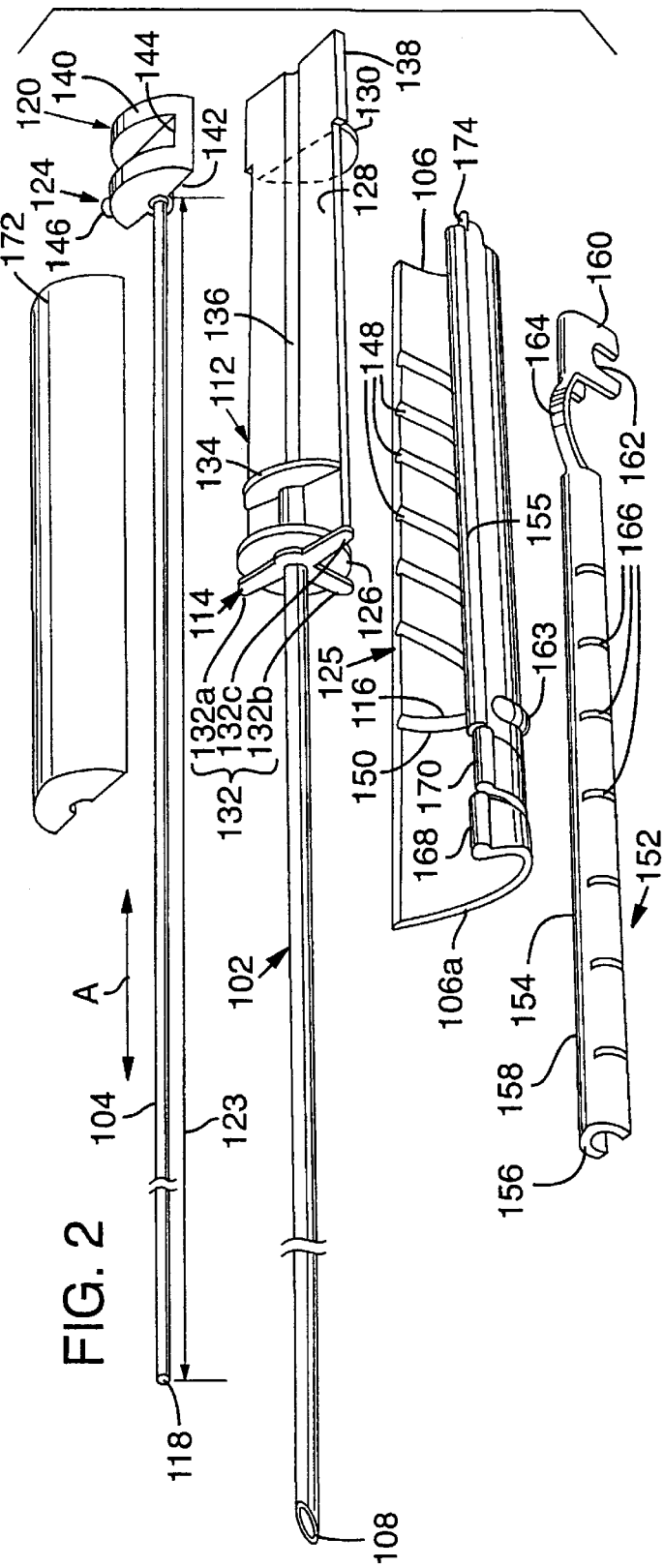

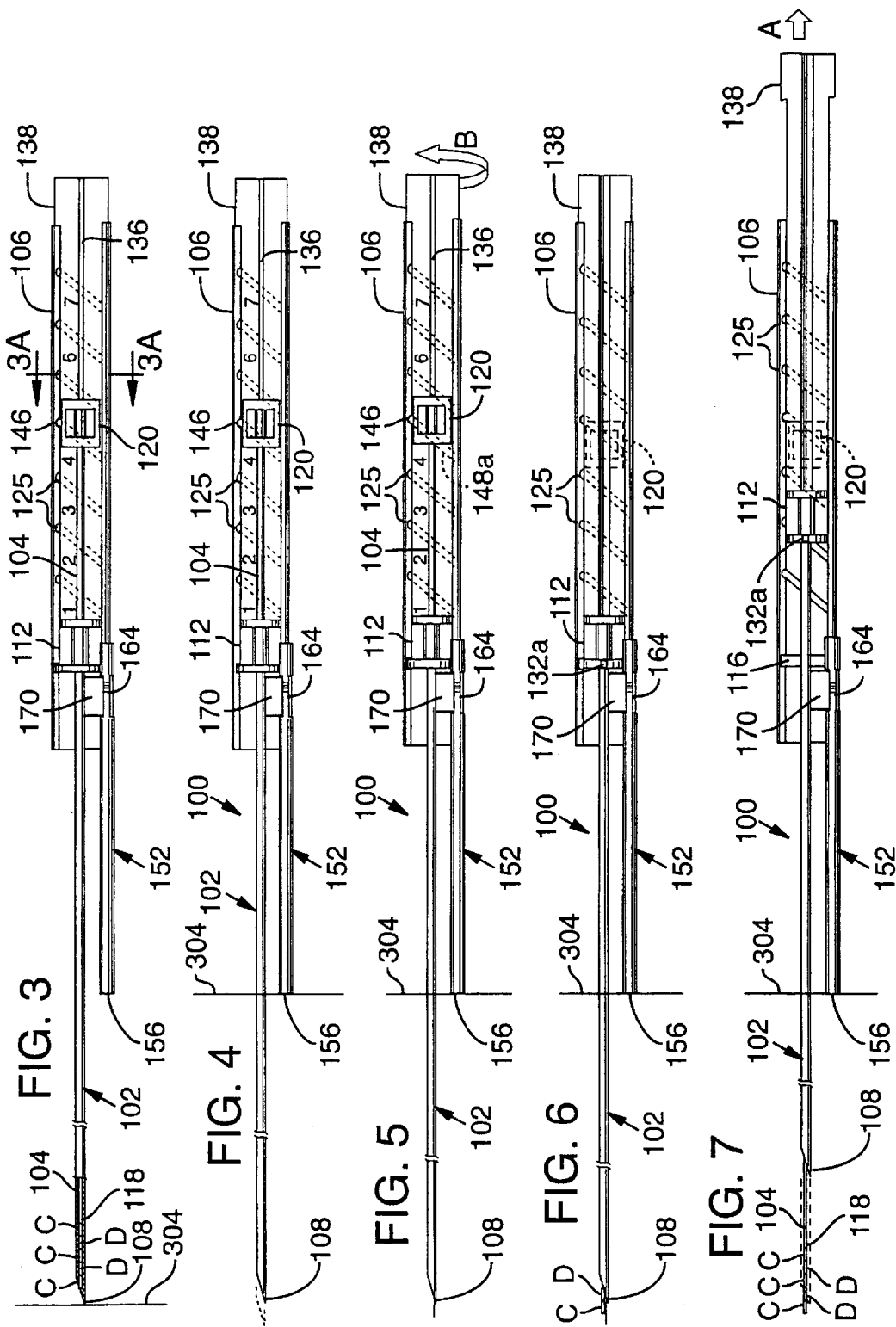

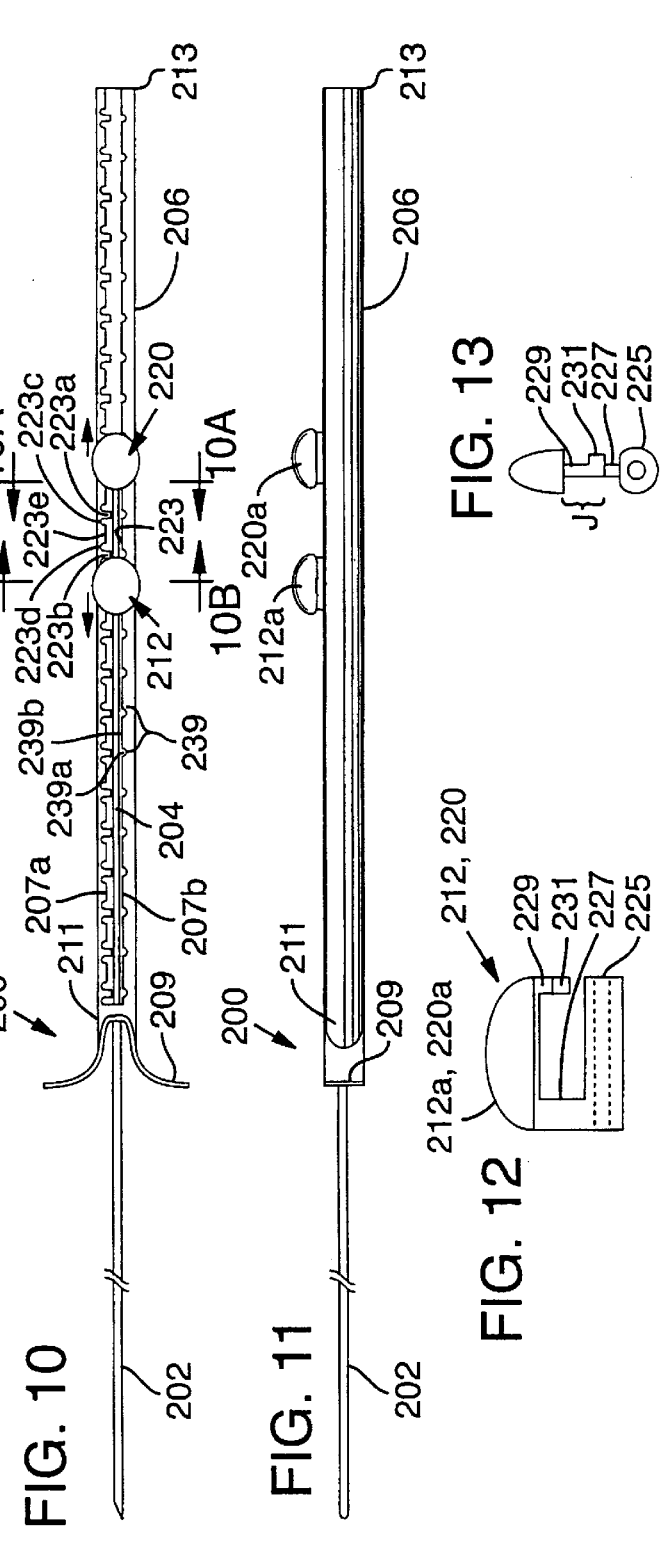

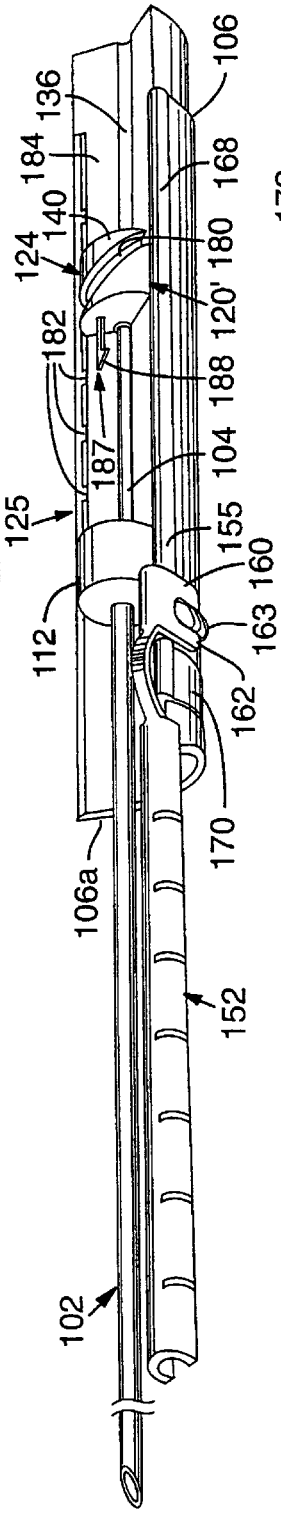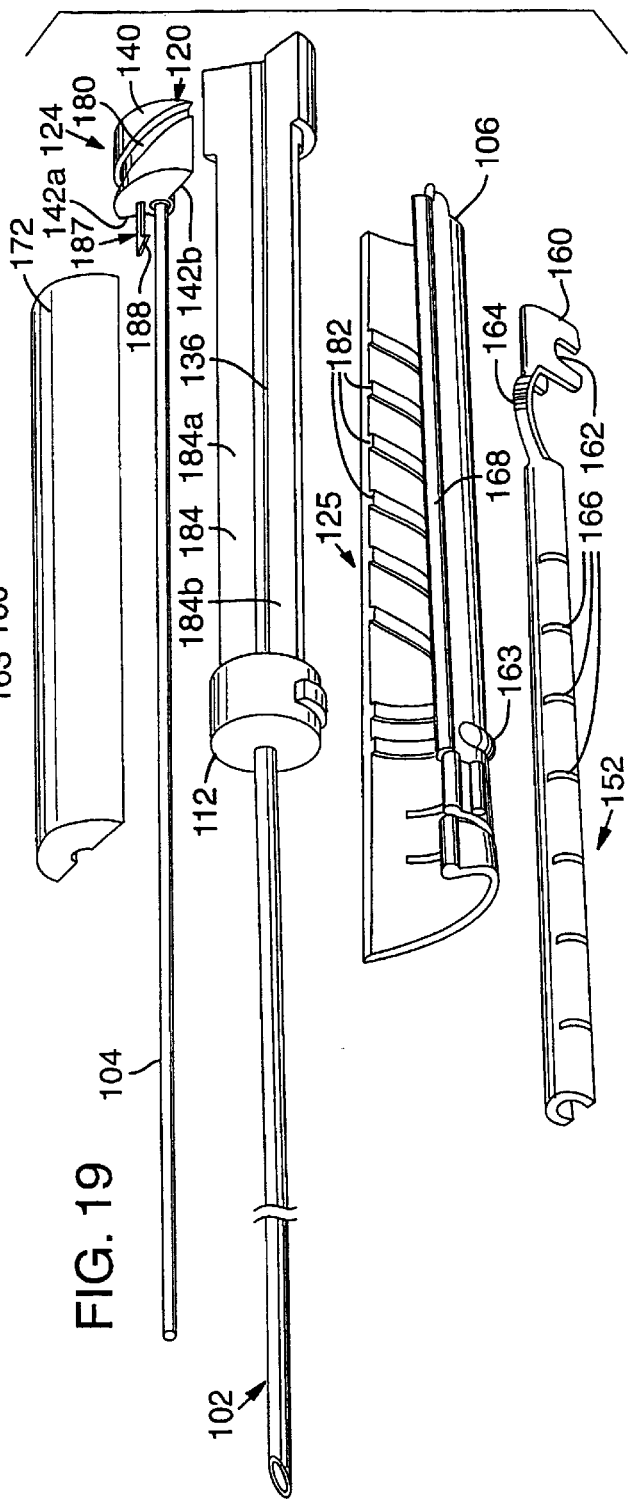
FIG. 18
FIG. 19

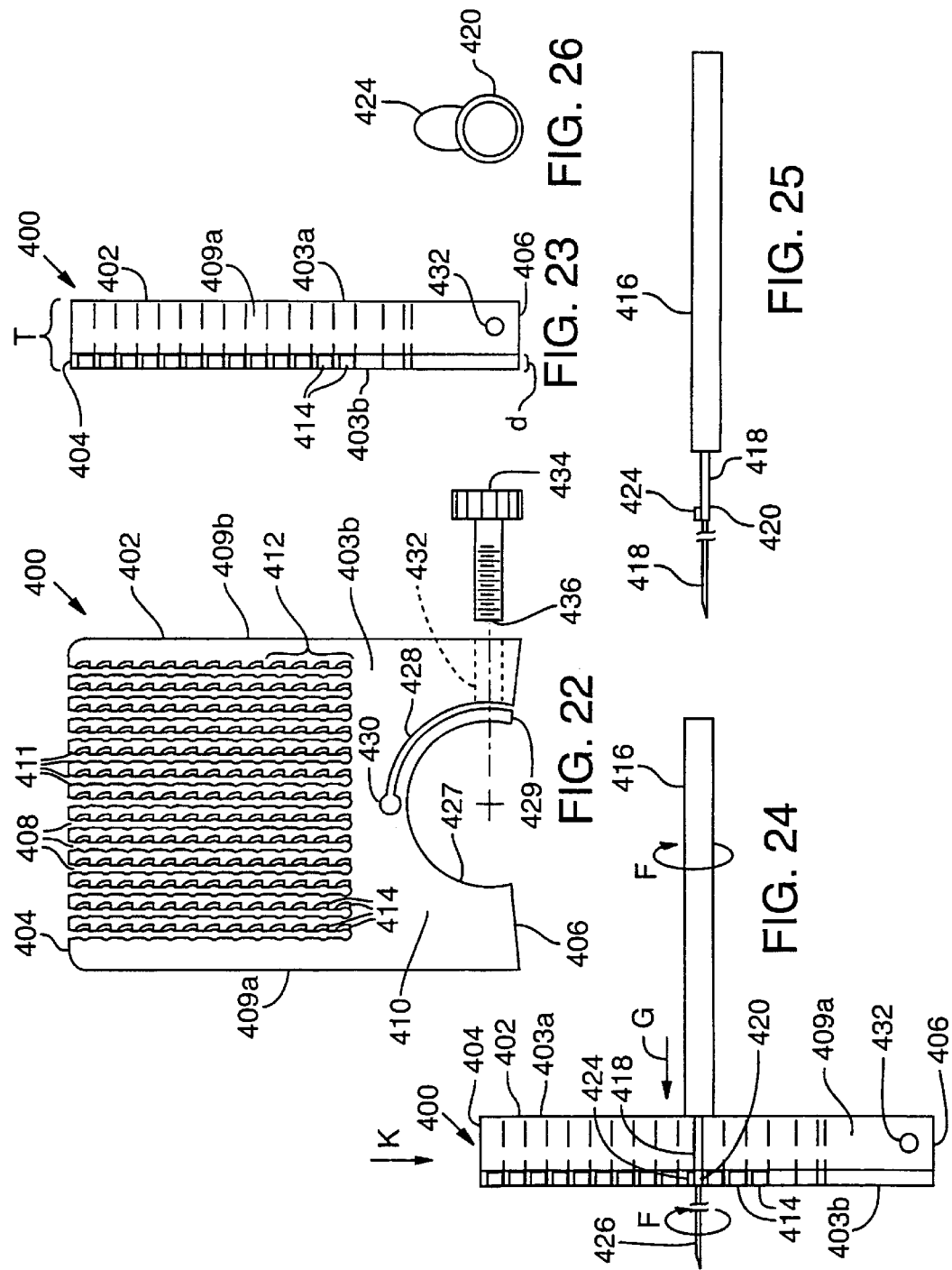

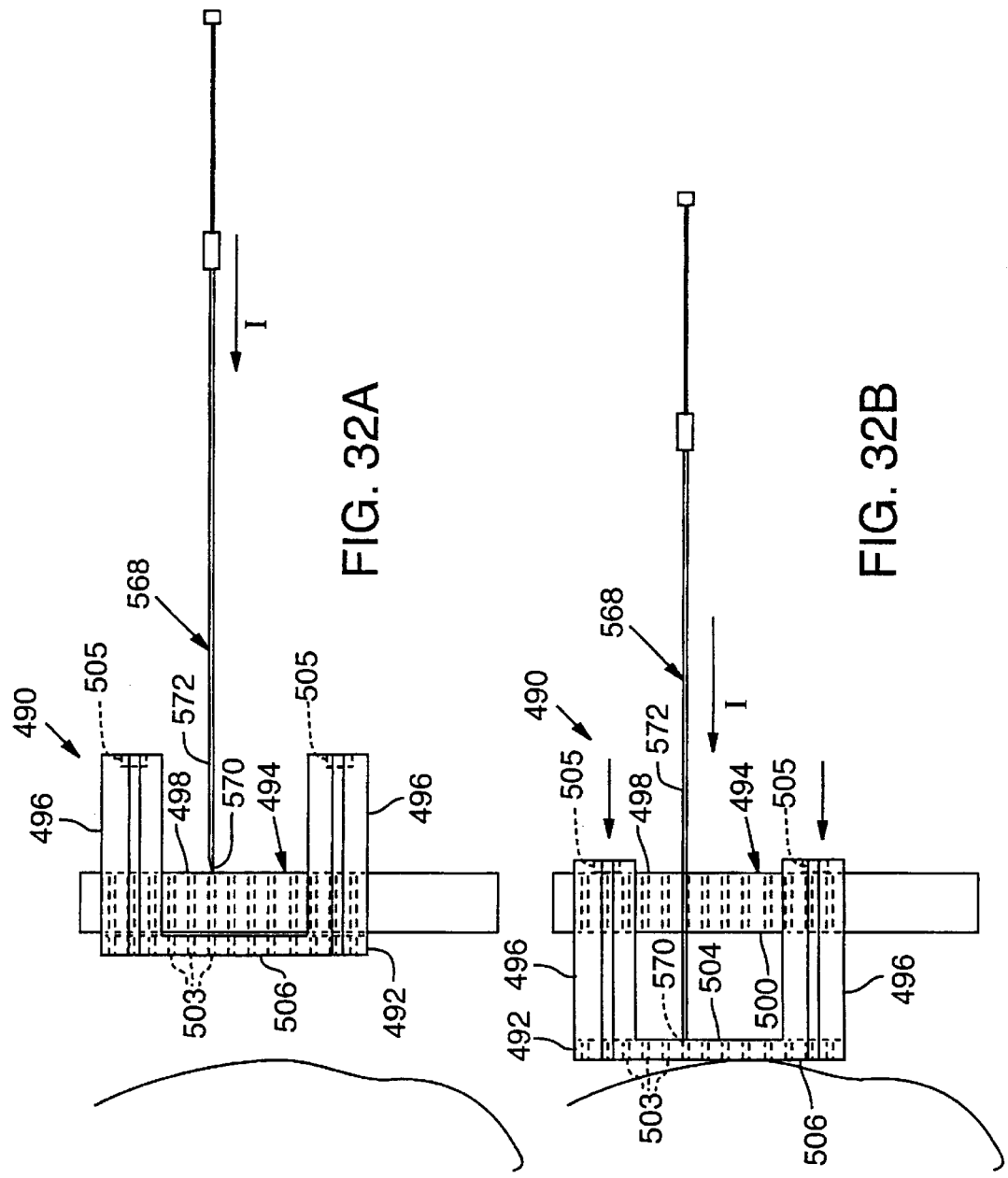

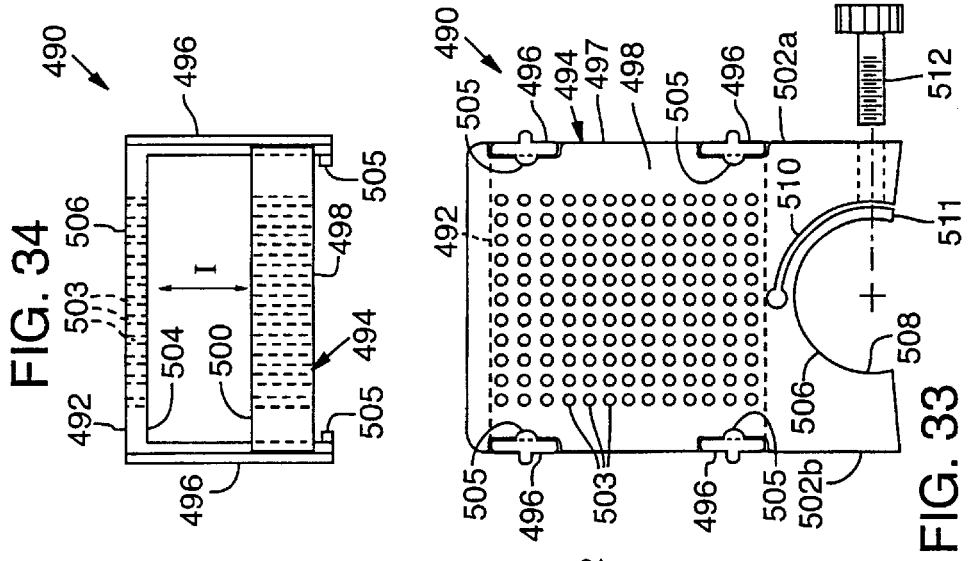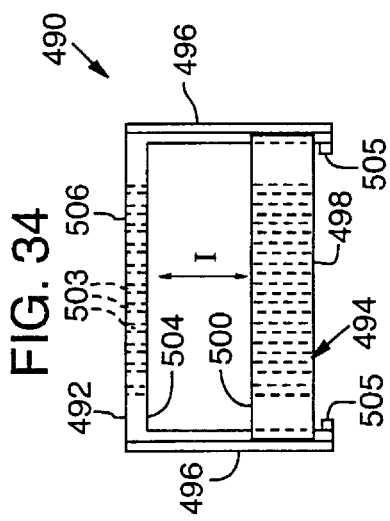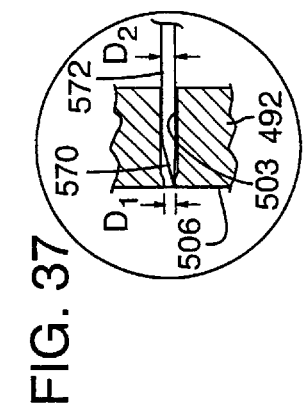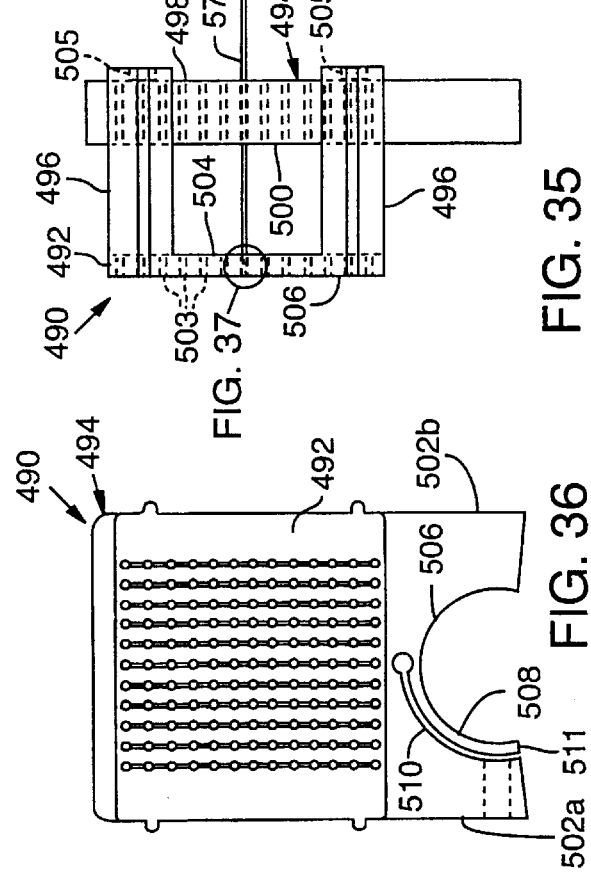

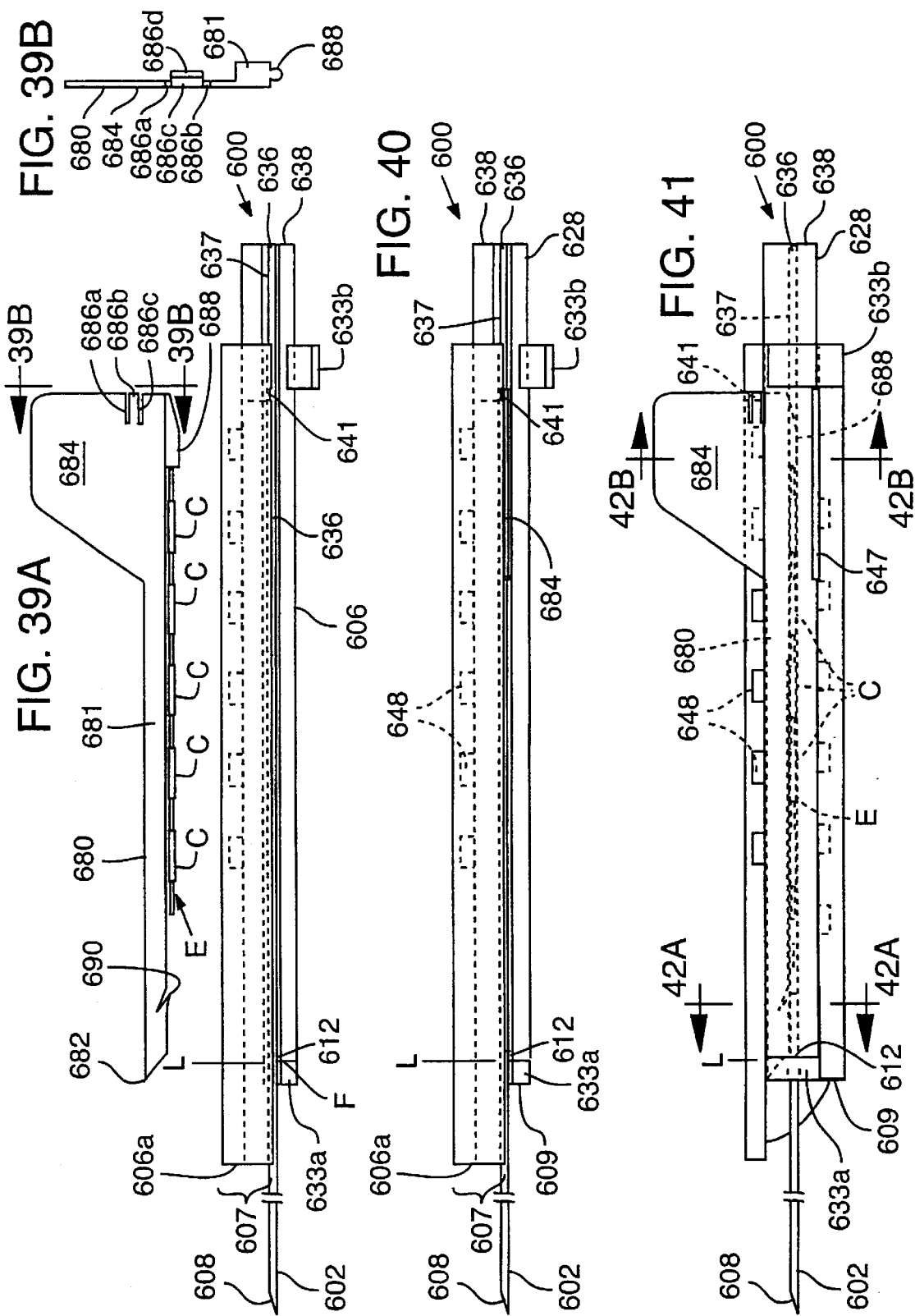

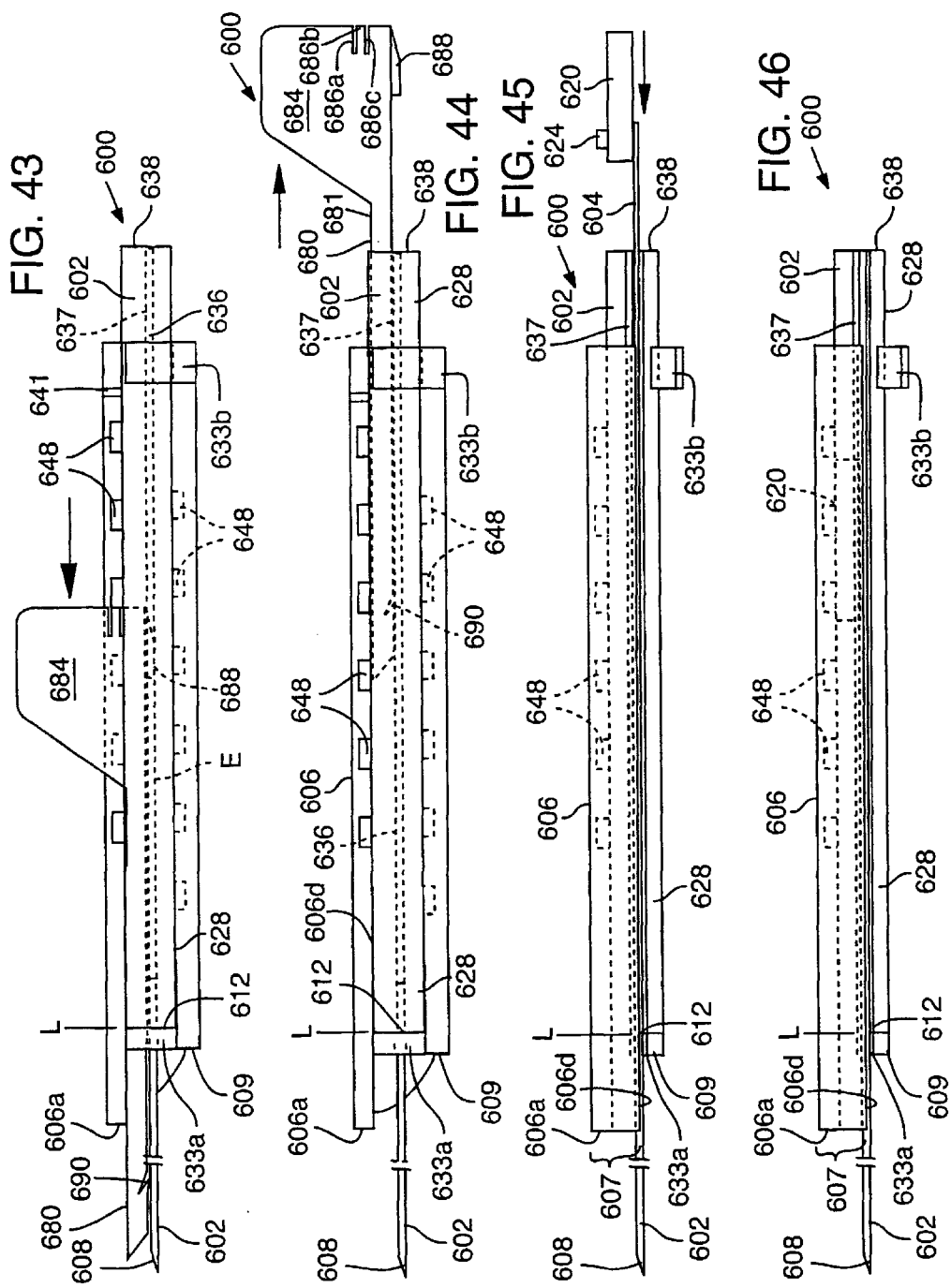

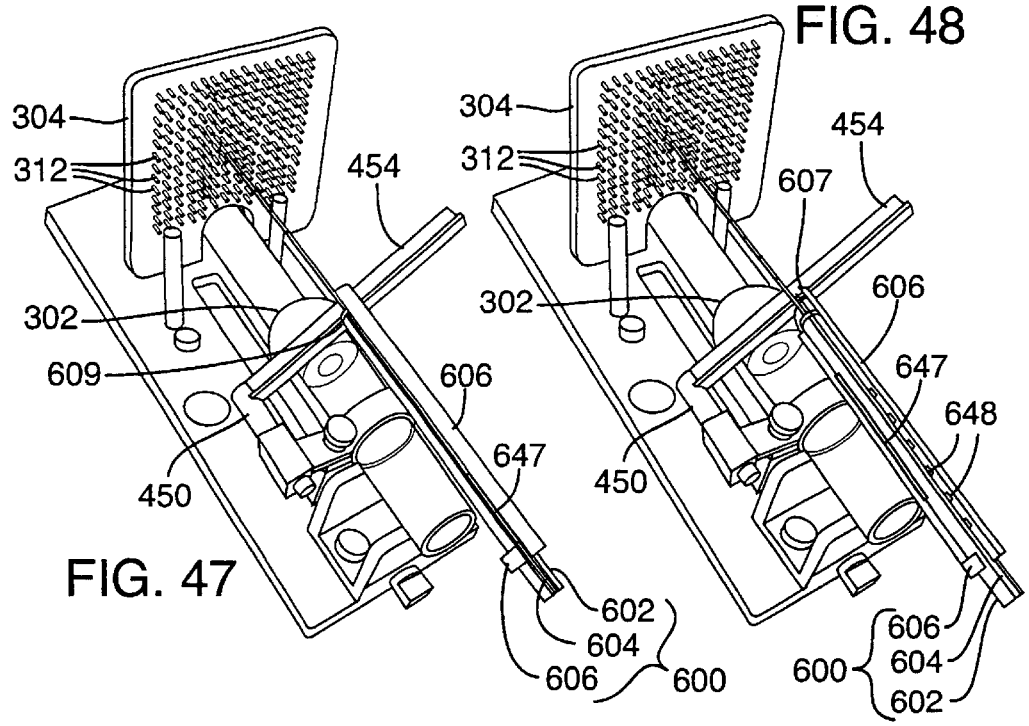
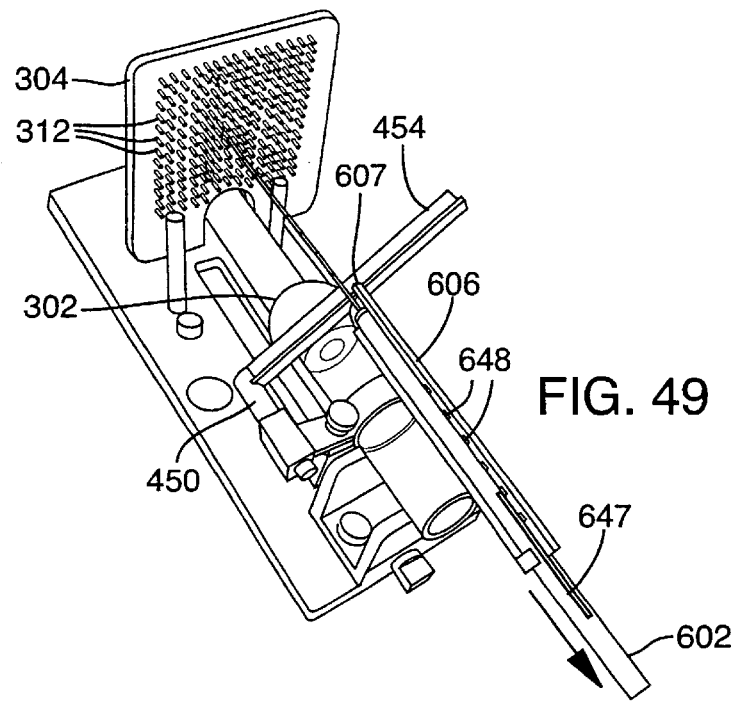

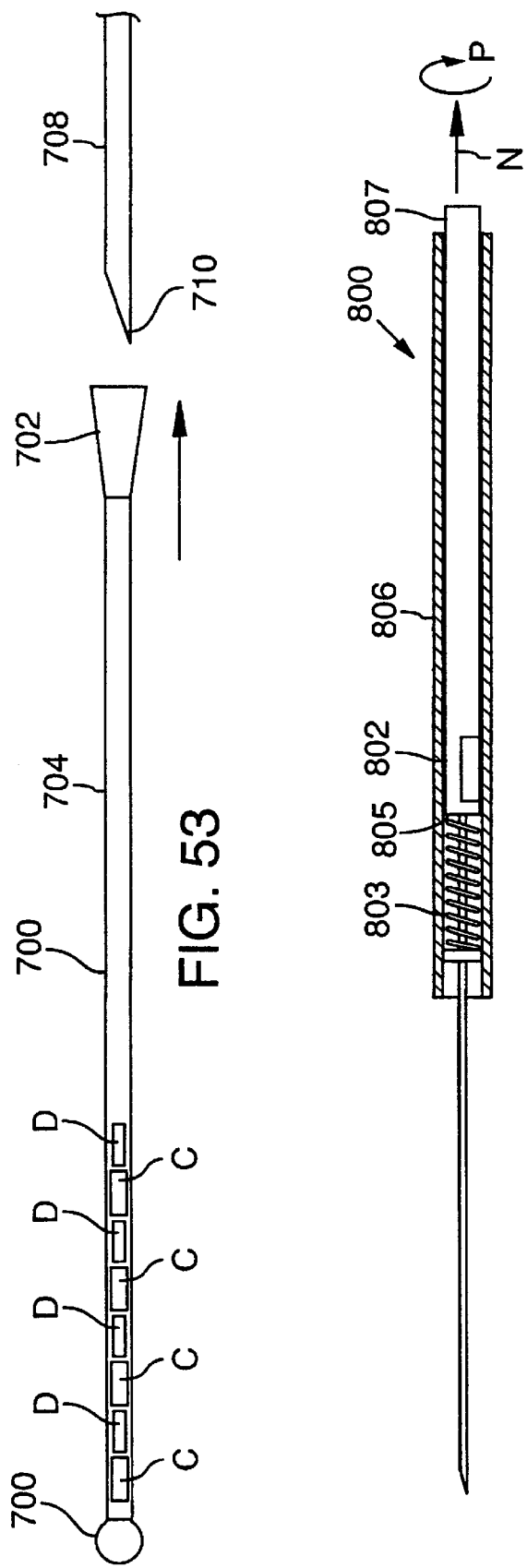

BRACHYTHERAPY INSTRUMENT AND METHODS

PRIORITY CLAIM

This application is a §371 U.S. national stage of PCT/US00/28668, filed Oct. 16, 2000, which was published in English under PCT Article 21(2), which in turn claims the benefit of U.S. Provisional Application Nos. 60/159,765, filed Oct. 15, 1999 and 60/200,596, filed Apr. 28, 2000.

FIELD

This invention relates to brachytherapy, and in particular to a brachytherapy needle assembly, needle stop and template.

BACKGROUND

Brachytherapy is a procedure for treating cancer by surgically implanting radioactive seeds within target tissue in an affected body part. Brachytherapy treatment can be used in treating prostate cancer, as well as other areas of the body in which radioactive sources can be implanted.

In a brachytherapy treatment for prostate cancer, the seeds are implanted into the prostate at precise locations defined on an x-y plane by pushing the seeds in a z direction through a hollow needle using a stylet inserted in the needle behind the last seed. The seeds are spaced from each other by one or more inert spacers that are implanted together with the seeds. In lieu of spacers, multiple seeds may be provided as a "strand" in which the seeds are connected together by a flexible shroud that is implanted with the seeds. In general, a series of aligned seeds is introduced with each insertion of the needle. The seeds must be accurately placed within the prostate to ensure satisfactory results.

In some brachytherapy devices, seeds are implanted by introducing them into a needle and inserting a stylet in the needle to advance the seeds to the tip of the needle. The needle is then inserted into the target tissue (such as the prostate), and the needle withdrawn while the stylet is held stationary, to unsheath and thereby implant the seeds in the tissue.

SUMMARY OF THE DISCLOSURE

In practice, it is difficult to hold the stylet stationary relative to the needle while the needle is being withdrawn to implant the seeds. It is also difficult to determine the starting position for seed delivery (which may be measured relative to the needle tip), and to implant the first seed at that pre-selected position. Even small unintended movements of the stylet relative to the needle, or a slightly inaccurate starting position, can result in inaccurate placement of the seeds, and less effective treatment. Another problem is that the needle frictionally engages the tissue into which it is placed, so that tissue deformation occurs as the needle is withdrawn.

Certain problems associated with the conventional devices used in brachytherapy procedures are overcome by at least some of the instrument embodiments disclosed herein. In particular embodiments, axial movement of the stylet is selectively controlled to diminish inaccurate positioning of the seeds, for example, by selectively fixing axial movement of the stylet relative to the needle or an instrument housing.

According to one disclosed embodiment, the brachytherapy device includes an elongated needle having a sharp end for insertion into target tissue, an elongated stylet which can slide through the needle, and a housing that selectively engages the needle and stylet to selectively fix the needle and stylet against axial movement, while allowing the needle to selectively move axially relative to the stylet when the stylet is fixed against axial movement, and allowing the stylet to selectively move axially relative to the needle when the needle is fixed against axial movement.

In particular embodiments, the housing independently selectively engages the needle and stylet, while in other embodiments the housing disengages the needle while simultaneously engaging the stylet. Certain embodiments of the housing can also selectively engage and disengage the needle in response to relative rotation between the needle and the housing or between the stylet and the housing. Alternatively, relative rotation between the needle and the housing selectively disengages the needle from the housing, and the same relative rotation that disengages the needle also engages the stylet to the housing. Relative rotation refers to movement of the housing relative to the needle or stylet, or rotation of the needle or stylet relative to the housing.

In other examples, the housing, the needle and the stylet are provided with cooperating members that interact to selectively fix the needle and stylet against axial movement. Examples of such cooperating members are a groove and a projection which slides into the groove. For instance, there may be a separate needle groove and stylet groove, with the stylet groove angled to advance the stylet in response to relative rotation between the stylet and the housing. Advancement of the stylet occurs as the projection moves into the angled groove and undergoes both rotation and slight axial displacement. A plurality of different parallel, non-communicating stylet grooves may be provided, so that the stylet can be fixed at a variety of preselected positions along the housing. In contrast, the needle groove can be contained in a plane perpendicular to a direction of axial movement of the needle in the housing, such that rotation of the needle or housing does not axially advance the needle relative to the housing, if such advancement is not desired.

In some embodiments, the projection comprises a projection from the needle that rotates into engagement with a groove (such as a thread in the inner wall of the housing) to selectively fix the needle against axial movement relative to the housing. Alternatively, the groove may be a gap in a stop collar that limits axial movement of the needle relative to the housing, except when the projection from the needle aligns with the gap in the stop collar. When the projection is aligned with the gap, the needle may be withdrawn axially by sliding the projection through the gap.

In yet another disclosed embodiment, the cooperating members that fix axial movement of the stylet and needle are independent triggers carried by each of the stylet and needle. The triggers are independently actuated to move the stylet or needle (or both) relative to the housing. The trigger may be a deformable detent associated with each of the stylet and needle, and the deformable detent is biased to engage the housing. However, the deformable detents of each trigger may be moved out of engagement with the housing to move the stylet or needle to which the trigger is attached. In particular examples, the housing includes a longitudinal slot having teeth along both longitudinal edges of the slot. Both of the separate triggers project out of the housing through the slot, and are biased into engagement with the teeth along the slot. However, the triggers can be moved away from the teeth to free the trigger for longitudinal movement in the slot. Movement of each trigger also moves the associated needle or stylet axially in the housing.

The instrument may be provided with a spacer extending from a distal end of the instrument, and a length of the spacer may be selectively altered to set a spacing distance between a distal tip of the instrument and a stop surface against which the spacer rests. A stop member can also be provided that opposes advancement of the needle along the path of insertion beyond a preselected distance. For example, the stop member can have an aperture or notch sufficiently large to permit the needle to pass through, but which is sufficiently small to prevent an enlarged diameter portion of the instrument to pass through. This arrangement prevents advancement of the needle beyond a preselected distance. The needle can be provided with a mating member that mates with the stop to resist rotation or axial movement of the needle. For example, the mating member can be engaged by rotating the needle to move a projection from the needle into a receptacle (such as an arcuate notch) on the stop member. In a particular embodiment, the stop member is a stop plate which includes a series of slots with notches at pre-selected positions in which the needle can seat.

The stop member may interfere with a clear view of a target area into which the needle is to be inserted. It is therefore sometimes advantageous for the stop member to be movable so that it can be selectively aligned with the path of insertion, or moved out of the path of insertion to provide a more unobstructed view when the guide function of the stop member is not required. The stop member can be made pivotable to facilitate movement of the stop member in and out of the field of view along the path of insertion of the needle. For example, in some embodiments the stop member is a pivotable arm having a plurality of notches that are selectively alignable with a template position through which the needle is to be inserted. When the pivotable arm pivots in a plane substantially perpendicular to the path of insertion and parallel to the plane of the template, the notches can be selectively aligned with almost any x-y position in the template by selecting a particular notch with the arm at a particular pivot angle.

In yet other described embodiments, the stop member includes a proximal stop member and distal stop member, such as a pair of parallel stop plates, that are movable apart from one another along the path of insertion of the needle to a limit distance. The proximal and distal stop plates have aligned apertures or notches through which the needle may be inserted, and the apertures or notches of the distal stop plate are smaller than the apertures of the proximal stop plate, so that advancement of the needle along the path of insertion moves the distal stop plate away from the proximal stop plate. However, the apertures or notches of the distal stop plate are deformable to allow the needle to be inserted through the distal stop plate by the application of sufficient insertion force after the distal stop plate reaches the limit distance. The non-deformed apertures or notches in the distal stop plate appear as a partial occlusion of the corresponding aperture or notch in the proximal stop plate. Deformation of the aperture or notch in the distal stop member provides a visible cue that the aperture or notch has already been used, because its enlargement will be visible through the corresponding notch in the proximal stop plate.

In yet other embodiments, the brachytherapy device has a housing that selectively engages the needle and stylet to selectively fix the needle and stylet against axial movement, wherein relative rotation between the housing and needle selectively engages the needle to the housing to fix the needle against axial movement relative to the housing, and relative rotation between the housing and the stylet selectively engages the stylet to the housing to fix the stylet against axial movement relative to the housing. Likewise, relative rotation between the housing and the needle selectively disengages the needle from the housing to permit axial movement of the needle relative to the housing, and relative rotation between the housing and the stylet selectively disengages the stylet from the housing to permit axial movement of the stylet relative to the housing. In particular embodiments, the same relative rotation between the housing and the needle that selectively engages the needle to the housing also disengages the stylet from the housing.

In those embodiments in which rotation of the needle relative to the housing is used to selectively engage or disengage the needle from the housing, rotation of the needle reduces frictional engagement between the needle and the target tissue. This reduction in frictional engagement permits the needle to be withdrawn from target tissue (such as an organ) more easily, without deforming the target tissue. Adherence of the needle to, for example, prostate tissue as the needle is withdrawn can deform the prostate, and interfere with the precise placement of radioactive seeds for the treatment of tumor loci.

Recitation of any aspect of a device in this Summary of the Disclosure is not intended to imply that the aspect is an essential element. This Summary is instead provided to facilitate understanding of the following detailed description.

BRIEF DESCRIPTION OF THE DRAWINGS

FIG. 1 is a perspective view of a first embodiment of the needle assembly according to the invention.

FIG. 2 is an exploded perspective view of the needle assembly of FIG. 1.

FIGS. 3–7 are various schematic side views of the needle assembly of FIG. 1 together with a template, showing various steps performed during use of the needle assembly.

FIGS. 8 and 9 are top views of the needle assembly of FIG. 1 showing use of the needle assembly during a seed loading operation before installation of a seed loading cover.

FIGS. 10 and 11 are top and side views, respectively, showing a second embodiment of the needle assembly.

FIGS. 12 and 13 are side and front views, respectively, of one of the knobs used to move the needle and stylet of the second embodiment.

FIG. 18 is a perspective view of the first embodiment of the needle assembly of FIGS. 1–2 showing alternative aspects.

FIG. 19 is an exploded perspective view of the needle assembly of FIG. 18.

FIG. 22 is a distal side view of a stop plate.

FIG. 23 is a left side view of the stop plate of FIG. 22.

FIG. 24 is a side view of a needle inserted through an aperture of the stop plate and rotated into engagement with the stop plate.

FIG. 25 is a side view of the needle of FIG. 24 showing a tab by which the needle can be engaged with the stop plate.

FIG. 26 is a magnified end view of the needle shaft showing the tab.

FIG. 32A is a side view of a template assembly with a movable plate initially positioned adjacent a distal side of the template showing a needle ready for insertion through the template.

FIG. 32B is a side view similar to 32A showing the needle after insertion through the template and the movable plate, with the movable plate in its fully extended position.

FIGS. 33, 34, 35 and 36 are proximal side, top, left side and distal side views, respectively, of the template assembly of FIGS. 32A and 32B.

FIG. 37 is a magnified side sectional view of one of the apertures in the movable plate.

FIG. 39A is a top view of an alternative first embodiment of the needle assembly showing a separate pusher and a seed strand used with the assembly.

FIG. 39B is an end view of the pusher viewed from the arrow 39B in FIG. 39A.

FIG. 40 is another top view similar to FIG. 39A, except showing the pusher coupled to the needle assembly and locked in place.

FIG. 41 is a side view of the needle assembly and pusher of FIG. 40.

FIG. 43C is a sectional view similar to FIG. 43B, except without the pusher and showing the needle rotated to a position to be retracted from the housing.

FIG. 43 is a side view of the needle assembly similar to FIG. 41, except the pusher has been unlocked and advanced to load the seeds into the needle.

FIG. 44 is side view of the needle assembly similar to FIG. 43, except the pusher has been retracted.

FIG. 45 is a top view of the needle assembly similar to FIG. 44, except that the pusher has been removed and the stylet has been inserted into the needle.

FIG. 46 is a top view of the needle assembly similar to FIG. 45, except the stylet has been advanced and engaged with the housing at a predetermined position.

FIG. 47 is a perspective view of the needle assembly of FIG. 46 during a procedure shown in relation to a stepping apparatus, with the needle inserted through an aperture in the template, and a step formed in the housing in contact against a stop to position the needle tip at the predetermined over-insertion depth.

FIG. 48 is another perspective view similar to FIG. 47, except showing that the needle assembly has been retracted and rotated such that the distal end of the housing is in contact against the spacer to position the needle tip at the predetermined insertion depth.

FIG. 49 is another perspective view similar to FIG. 48, except showing the needle being retracted to implant the seeds while the housing remains in contact against the spacer.

FIG. 53 is a schematic side view of an auxiliary seed loader shown in relation to a needle shaft into which seeds are to be loaded through the needle tip.

FIG. 54 is a schematic side view of a needle assembly having a spring-activated seed implanting feature.

DETAILED DESCRIPTION OF SPECIFIC EXAMPLES

Figure 3A:
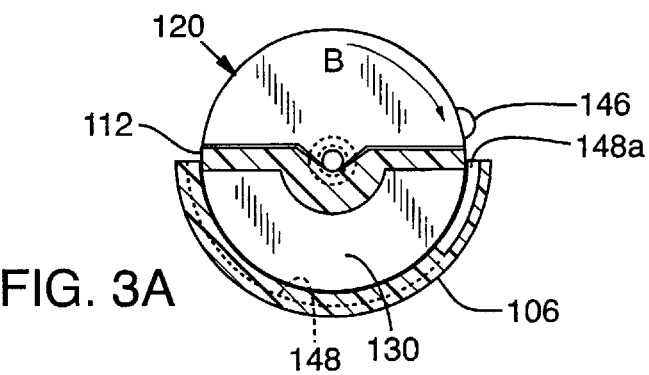
FIG. 3A is an end cross-sectional view of the needle assembly of FIG. 3 taken along the line 3A—3A of FIG. 3.

According to some disclosed embodiments of the implantation device, a housing serves to couple the needle and the stylet together to assist in coordinating axial movement of the needle and stylet relative to each other. The stylet, which slides within the needle, is provided with a stylet hub that can be selectively engaged with the housing. When the stylet hub is not engaged with the housing, the stylet can be moved (e.g., by axial sliding) relative to the housing. When the stylet hub is engaged with the housing, the stylet cannot be moved relative to the housing in the axial direction.

Similarly, the needle can be selectively engaged with the housing, for example by a needle hub or a rib on the needle body. When the needle hub or rib is engaged with the housing, the needle cannot be axially moved relative to the housing. When the needle hub or rib is not engaged with the housing, the needle can be moved (e.g., by sliding) relative to the housing in the axial direction. This arrangement helps control axial positioning of the stylet, to improve initial needle positioning, initial seed placement, and subsequent seed and spacer placement, with less chance of error compared to conventional devices.

In specific implementations, relative rotation between the housing and the needle and/or stylet controls the axial positioning. Although specific examples in this specification will describe rotation of the needle and stylet, rotation of the housing relative to the needle and/or stylet will achieve a similar effect. However, for purposes of simplifying explanation, specific examples will be described in which the needle and/or stylet rotates.

The needle may be rotated prior to and/or during its retraction relative to the stylet that implants the seed, to engage the needle with the housing and inhibit axial movement of the needle. This rotation of the needle tends to decrease the friction between the outer surface of the needle and the surrounding tissue, thus resulting in easier subsequent withdrawal of the needle from the tissue, with less chance of moving the implanted seeds from their desired positions.

Advantageously, the housing can be sized to have a length (typically less than about 6 cm) that can be accommodated within a standard needle box. In this way, the assembled instrument (i.e., housing with needle and stylet inserted therein) can be transported and/or stored in a standard needle box.

According to one example, the needle and the stylet are each engageable with the housing by rotation. In particular examples, the needle and stylet are each independently engageable with the housing. The stylet rotates with the needle, and the needle and the stylet are configured to be engaged with the housing over juxtaposed portions of a rotation. Therefore, the same rotation of the needle that engages the stylet with the housing also disengages the needle from the housing, for example at the end of that rotation. Thus, there is a portion of that rotation over which the stylet and the needle are each engaged with the housing, which is useful as a safety feature (e.g., in preventing inadvertent axial movement of the needle or the stylet when the needle assembly is stored) and in positioning the needle tip at an over-insertion depth. In such particular examples of the instrument, the one piece, unitary nature of the device facilitates one-handed manipulation and operation during the brachytherapy procedure.

The stylet is movable relative to the needle and the housing, for example moving axially forward to implant the most distal first seed beyond the needle tip. The needle is also movable relative to the stylet and the housing, for example moving axially rearward to implant the remaining seeds and spacers as the needle is withdrawn over a stationary stylet to unsheath the seeds.

The instrument may also be provided with a separate pusher used to secure the seeds within the assembly prior to use (or even during transport), and to load the seeds into the needle for subsequent implantation.

As used in the specification, "distal" refers to a portion of the instrument that is relatively closer to the patient, while "proximal" refers to a portion of the instrument that is relatively closer to the operator of the instrument.

Conventional Brachytherapy System

Figure 17:
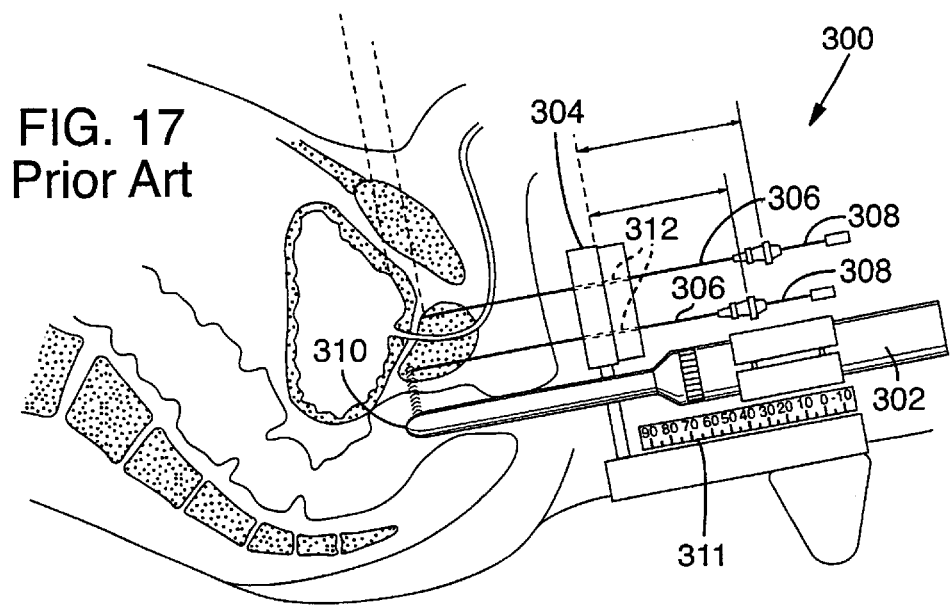
FIG. 17 is a side view of a brachytherapy assembly with a conventional needle and stylet arrangement, schematically showing a cross-section of a male pelvis into which the assembly is introduced.

The disclosed instrument can be used for implantation of therapeutic particles in many organs. However, to facilitate explanation of the device, it will be disclosed in connection with the delivery of radioactive seeds to a human prostate. Referring to FIG. 17, a conventional brachytherapy system 300 includes a stepping unit 302, a template 304, one or more needles 306 and a corresponding number of stylets 308. U.S. Pat. No. 5,871,448 discloses another example of a conventional stepping unit.

As illustrated in FIG. 17, an ultrasound probe 310 coupled to the stepping unit 302 is inserted rectally to a depth adjacent a portion of a patient's prostate P. The ultrasound probe 310 emits waves directed through the adjacent portion of the prostate P from which an ultrasonic cross-sectional image of that portion of the prostate P can be obtained. The stepping unit 302 incrementally moves the ultrasound probe to obtain ultrasound images of successive planes of the prostate or other organ or tissue. The stepper unit 302 includes a scale 311 oriented in the z direction that shows the depth of the ultrasonic probe 310 relative to a predetermined datum.

The template 304 is supported by the stepping unit 302 at a position adjacent but spaced from the patient's body. The template 304 has a matrix of apertures 312, usually defining an x-y array, each of which apertures 312 is sized to receive one of the needles 306. The apertures 312 extend in rows oriented in the x direction (i.e., perpendicular to the drawing page) and in columns oriented in the y direction (i.e., in or parallel to the plane of the drawing page and parallel to the substantially vertical edges of the template 304). Thus, each aperture 312 corresponds to a precise location in the x and y directions on a cross section of the prostate P parallel to the template 304. Accordingly, for any specific aperture, a particular configuration of seeds for treating a portion of the prostate P at a position corresponding to that aperture can be used.

The template 304 is positioned at a known point in the z direction to provide a two-dimensional representation of the location of the patient's prostate P. Even if the precise location in the x and y directions is known, the desired position of the seeds in the z direction must be determined. The z direction position of a particular seed represents the depth at which that seed will be implanted in the housing relative to a known reference. In a typical procedure, a plurality of seeds are implanted in the patient's body along an axis extending in the z direction (the axial direction with respect to the brachytherapy instrument) throughout the depth of the prostate P.

These seeds are usually preloaded, together with the spacers that separate the seeds, into the hollow needle 306. The stylet 308 is then inserted into the needle 306 with the tip of the stylet 308 abutting the most proximal or last seed or spacer. The tip of the needle 306 is typically sealed with a plug of bone wax (not shown) that prevents the seeds from inadvertently falling out of the needle 306.

Prior to implantation, the location of the prostate P and the tip of the needle 306 are determined using the ultrasound probe 310. The feedback from the ultrasound probe 310 allows the starting position to be determined.

During implantation according to one type of brachytherapy procedure, the stylet 308 is first moved slightly forward in the axial direction relative to the needle 306 to urge the most proximal seed forward, in turn moving the entire line of seeds and spacers within the needle 306 forward and dispensing the most distal seed from the needle 306 at the starting position in the prostate. Advancing the stylet in this way also generates a sufficient force to eject any bone wax plug from the needle tip. Thereafter, the needle 306 is withdrawn over the seeds to unsheath them while the stylet 308 is held in place, which implants the line of seeds and spacers in the prostate P from the starting position to a terminating position as desired.

In practice, however, it is difficult to hold the stylet 308 stationary relative to the needle 306 while the needle 306 is being withdrawn. In some cases, two individuals must hold and/or manipulate the various components. It is also difficult to determine the starting position, and to implant the first seed at that position. Even small unintended movements of the stylet 308 relative to the needle 306, or a slightly inaccurate starting position, can result in inaccurate placement of the seeds, and less effective treatment.

First Embodiment

FIGS. 1 and 2 show a first embodiment of an instrument 100 that includes a needle assembly with a hollow needle 102 within which a stylet 104 is partially inserted. The stylet 104 is dimensioned to slide within the needle 102 (which in this example is a hollow closed shank with a sharp open end). The needle 102 and the stylet 104 are each coupled to a housing 106, and are each selectively movable relative to each other and to the housing 106 in an axial direction A, as is described below. In the illustrated example, the housing is a one piece member that partially encloses the needle and stylet, and interacts with them for selective axial fixation of the needle and stylet. However in other examples, the housing may be more than one piece, and/or may enclose more or less of the stylet and needle. Some housings may not enclose the stylet and needle at all, but may instead extend parallel to them, while still providing the fixation function provided by the illustrated housing.

The needle 102 has a beveled needle tip 108 that, as illustrated, is spaced from a forward end of the housing 106 by a predetermined needle insertion length 110. A needle hub 112 is attached to the needle 102 at a proximal end (i.e., opposite the distal needle tip 108). The needle hub 112 has a needle/housing engaging feature 114, and the housing 106 has a corresponding needle receiving feature 116. When the needle 102 is assembled in the housing 106 as illustrated in FIG. 1, the needle/housing engaging feature 114 engages the needle receiving feature 116, and the needle 102 cannot be moved in the axial direction A relative to the housing 106. As described in more detail below, the needle/housing engaging feature 114 and the needle receiving feature 116 can be selectively disengaged (e.g., by rotating the needle 102 approximately 180 degrees in a direction B), thus allowing the needle 102 to be moved axially rearwardly relative to the housing 106.

As illustrated in FIG. 8, before a procedure is initiated, the needle 102 is provided with a predetermined number of radioactive seeds C. Adjacent seeds are separated by one or more inert spacers D, which in the disclosed embodiment are of equal lengths. Prior to the procedure, the stylet 104 is positioned as illustrated in FIG. 9 such that a stylet tip abuts the most proximal seed C or spacer D.

As shown in FIG. 2, the stylet 104 has a stylet hub 120 positioned at a proximal end of the stylet, at an end of the stylet opposite the distal stylet tip 118. The distance between a distal face of the stylet hub 120 and a forward projection 134 on the needle hub 112 defines a stylet insertion distance 122 (i.e., an axial distance that the stylet 104 will travel during a procedure before contracting the projection 134). An overall working length 123 of the stylet 104, i.e., from the distal face of the stylet hub 120 to the stylet tip 118, is dimensioned substantially the same as a length of the needle 102 (in this example from a proximal surface of the forward projection 134 to the needle tip 108).

The stylet 104 has a stylet/housing engaging feature 124, and the housing 106 has a corresponding stylet receiving feature 125. When the stylet 104 is assembled within the needle 102 and the housing 106 as illustrated, the stylet/housing engaging feature 124 and the stylet receiving feature 125 are not engaged with each other, and thus the stylet 104 can be moved relative to the housing 106 in the axial direction A. As illustrated, the stylet 104 can also be moved relative to the needle 102 in the axial direction A, particularly when the needle 102 is engaged with the housing 106. The stylet 104 can be selectively engaged with the housing 106 by engaging the stylet/housing engaging feature 124 and the stylet receiving feature 125, which in this disclosed embodiment is achieved by rotating the stylet in the direction B (FIG. 5) to the position shown in FIG. 6.

In the specific embodiment shown in FIG. 2, the needle hub 112 has a generally cylindrical needle hub portion 126 attached to the proximal end of the needle 102, and a substantially flat extension portion 128 extending rearwardly from the needle hub portion 126. Extension portion 128 presents a flat upper and lower face, and a semi-circular projection 130 extends from the lower face of the extension portion 128 at a proximal end of the needle hub 112.

The needle hub portion 126 has a plurality of radially extending wings 132. In the specific embodiment, three such wings 132a, 132b and 132c are shown extending radially from a center of the needle hub portion at approximately 9:00 o'clock, 3:00 o'clock and 6:00 o'clock positions, respectively.

A semi-circular projection 134, similar to the projection 130, extends from the upper face of the extension portion 128 adjacent the needle hub portion 126. In the disclosed embodiment, the needle hub portion 126 and projections 130, 134 are axially spaced and substantially parallel to one another.

The extension portion 128 includes a central longitudinal groove 136 extending in its upper face from the needle hub portion 126, through the projection 124, and to the proximal end of the needle hub 112. The groove 136 extends in the axial direction A and is sized to receive the stylet 104 therein, such that the stylet can slide within the groove 136.

As illustrated in FIG. 1, when the needle 102 is assembled within the housing 106, a proximal end 138 of the extension portion 128 extends rearwardly of the housing 106. The proximal end 138 is dimensioned larger than a distal end of the extension portion 128 that fits within the housing 106; in the illustrated embodiment the width of end 138 is wider than the distal end of housing 106 to act as a stop on inward axial movement of the needle 102 relative to the housing 106.

In the specific embodiment shown in FIG. 1, the stylet hub 120 is generally semicylindrically shaped with a rounded outer face 140 and a flat inner face 142. The inner face 142 is shaped to slide along the corresponding flat part of the extension portion 128 when the stylet 104 is moved relative to the needle 102. In the illustrated implementation, the stylet hub 120 has a transverse central notch 144 in the outer surface 140 positioned approximately midway along the stylet hub 120 in the axial direction A.

The housing 106 is channel-shaped with an arcuate cross-section transcribing slightly less than 180 degrees (see FIG. 3A). The housing 106 has an inner diameter that is dimensioned to allow the needle hub 112 to rotate therein by sliding upon the housing. The housing 106 has an inclined distal end 106a, a flat proximal end, and arcuate sides which partially surround the needle 102. A needle hub groove 150 is formed circumferentially in the inner surface of the housing 106 adjacent the forward end 106a, and extends in a plane transverse to the axial direction of the instrument. A series of parallel spaced or interrupted-threads 148, which extend at a constant pitch, are also formed in the inner surface of the housing 106. In a specific implementation, the pitch of the threads 148 is set such that adjacent threads are spaced at approximately 1 cm intervals. The series of threads 148 are placed rearwardly from and are angled to the needle hub groove 150. At the proximal end of housing 106, a rear catch 174 (FIG. 2) is attached to the housing 106 to prevent the needle hub 112 from being withdrawn rearwardly from the housing 106 in the axial direction A.

Needle/Housing and Stylet/Housing Engagement

As described above, the needle 102 and the stylet 104 are each selectively engageable with the housing 106.

In the specific implementation shown in FIGS. 1 and 2, the needle/housing engaging feature 114 is the wing 132b at the 6:00 o'clock position (FIG. 2). The needle receiving feature 116 is the needle hub groove 150 in the inner surface of the housing 106. When the needle 102 and the housing 106 are assembled together as shown in FIG. 1, the wing 132b is engaged in the needle hub groove 150, thus engaging the needle 102 and the housing 106 together and preventing relative axial movement between the needle 102 and the housing 106. The other wings 132a and 132c are positioned in contact with the sides of the housing 106, above groove 150.

The needle 102 and the housing 106 are disengaged by rotating the needle 102 approximately 180 degrees in the direction B as shown in FIG. 1 (e.g., by rotating the proximal end 138 of the needle hub 112) such that the wing 132b (FIG. 2) is disengaged from the needle hub groove 150. Wings 132a and 132c rotate through 180 degrees such that they switch positions from that shown in FIGS. 1 and 2. Once the wings are disengaged from the groove 150, the needle 102 can then be moved in the axial direction relative to the housing 106, and for example be moved proximally relative to the housing 106, while 132a and 132c slide along upper edges of the housing to stabilize retraction of the needle 102.

In the specific embodiment shown in FIGS. 1 and 2, the stylet/housing engaging feature 124 is a projection 146 extending from the stylet hub 120 adjacent the notch 144 which projects partially above the outer surface 140 of stylet hub 120. As illustrated, the projection 146 is a hemispherically shaped knob. The stylet receiving feature 125 on the housing 106 is the series of threads 148.

FIG. 1 shows the instrument before the stylet 104 is inserted in the housing 106. To engage the stylet 104 with the housing 106, the projection 146 is placed in an adjacent one of the threads 148, such that rotating the stylet 104 moves the stylet 104 axially relative to the housing 106.

The stylet 104 is rotated into engagement with the housing 106 by rotating the needle hub 112 in the direction B. The extension portion 128 of the needle hub 112 bears against the inner face 142 of the stylet hub 124, thus causing the stylet 104 to rotate by the same amount while the projection 146 engages and moves within one of the angled threads 148. Simultaneously, the wing 132b of the needle hub 112 is rotated out of the needle hub groove 150, and the wings 132a and 132c are positioned to slide along the upper edges of housing 106. Thus, the same rotation of the needle hub 112 that engages and advances the stylet 104 to the housing 106 also disengages the needle 102 from the housing 106 to allow axial movement of the needed over the stylet.

Axial Spacer

Optionally, the needle assembly 100 includes an axial spacer 152 that extends anteriorly from the instrument to help maintain the needle assembly 100 at a pre-selected axial position during use. The axial spacer 152 is coupled to the housing 106, and is movable relative to the housing 106 in the axial direction to permit the needle assembly to be positioned at a pre-selected distance from the target. The disclosed spacer slides along an upper edge of the housing 106 to selectively position the spacer.

In the specific implementation shown in FIGS. 1 and 2, the axial spacer 152 includes a spacer member 154 which couples with a rounded upper coupling edge rail 155 of the housing 106. The spacer member 154 has a distal end 156, a middle portion 158, and a proximal end 160. The spacer member 154 is channel-shaped, and its middle portion has a generally semicircular cross-section that can mate with and slide along the rail 155. A spacer lock 162 is provided at a proximal end of spacer 154, and engages a locking rib 163 that projects away from the housing 106. A spring arm 164 connects the spacer lock to the spacer 154.

The spacer member 154 has a series of regularly spaced indentations or perforations 166, to allow a distal portion of the spacer member to be broken off to select an appropriate length.

The housing 106 also includes a movable lockout tab 170 for engaging the spacer member 154 in an area adjacent the spring 164 arm. When the spacer member is fully extended in the axial direction A, i.e., when the spacer lock 162 abuts the lockout tab 170, the spring arm 164 is aligned with the lockout tab. The functions of the spring arm 164 and the lockout tab 170 are described below.

The axial spacer 152 is retractable, in that it can slide rearwardly over the guide rail 155 to rest in place within the length of the housing 106, for example to allow storage of the needle assembly 100 in a conventional needle rack. Alternatively, the axial spacer 152 could be connected by a hinge to a distal end of the housing 106 to allow it to be pivoted and locked in an extended position during use, and unlocked and folded into a storage position against the housing 106 when not in use. In addition, although the axial spacer 152 as illustrated is spaced from the axis defined by the needle 102, the spacer 152 could be axially positioned such that the needle 102 extends through the spacer 106.

Seed Loading Cover

Optionally, a removable seed loading cover 172 may be provided for the instrument, as shown in FIGS. 1, 2, 8 and 9, to facilitate placing seeds C and the spacers D into the needle 102. As illustrated in FIGS. 1, 2 and 8, the cover 172 has an arcuate shape and fits over the body 128 of the needle hub 112, and mates with the upper edges of the housing 106.

During loading, cover 172 and stylet 104 are removed from the needle assembly 100. A predetermined number of seeds C and spacers D are alternatingly deposited in the groove 136 of housing 128 (FIG. 8),and the stylet 104 is inserted into and slid forwardly through the groove 136 (FIG. 9) and into the needle 102, to complete the loading operation.

Operation

The operation of the needle assembly 100 in conjunction with certain elements of the brachytherapy system 300 of FIG. 17 is described below in connection with FIGS. 3–7. In the following description, the needle assembly 100 includes the axial spacer 152 that has been set to a predetermined length.

In FIG. 3, the needle assembly 100 is illustrated prior to insertion through a desired one of the apertures in the template 304. The needle 102 has been previously loaded with seeds and spacers, and the stylet 104 is positioned such that the stylet tip 118 abuts the last seed or spacer. The needle 102 has been rotated slightly (e.g., by about 10 degrees) to cause the stylet 104 to engage the housing 106, temporarily preventing axial movement between the needle 102 and the stylet 104.

As shown, a forward end of the stylet hub 120 is aligned with the numeral "4" in the legend extending along the housing 106. Thus, in this example, the stylet 104 is positioned 4 cm from the proximal surface of the needle hub portion 112.

In FIG. 4, the needle assembly has been inserted into the template 304 (as in FIG. 17), and the position of the needle tip 108 is verified with images obtained by the ultrasound probe 310. To verify the needle tip position, the spring arm 164 (FIG. 4) is flexed, which allows the needle tip 108 to advance axially forward slightly to an "over-insertion depth," as shown in dashed lines. This forward movement of the needle tip 108 appears on the ultrasound image of a cross section of the prostate P at the starting position. In specific embodiments, the over-insertion depth is set at about 1 cm deeper than an "insertion" depth, i.e., the depth of the needle with the spring arm 106 in its unbiased position, where the implanting of seeds and spacers is commenced.

FIGS. 5 and 6 show the process of implanting the seeds and spacers at the insertion depth. The proximal protruding end 138 of the needle hub 112 is rotated while the needle assembly 100 is held in place with the spacer 152 against the template 304 (FIG. 17). The end 138 is rotated 180 degrees, which advances the stylet 104 within the housing 106 by moving the projection 146 along one of the threads 148 to force the stylet distally as the stylet 104 rotates. Distal advancement of the stylet 104 advances the most proximal seed forward, which moves the entire line of seeds and spacers in the needle 102 axially forward, and advances the most distal fist seed out of the needle tip 108. The first seed is implanted just forward of the position of the needle tip 108, i.e., in the ultrasound cross-section image as desired in certain brachytherapy procedure protocols.

FIG. 7 illustrates implantation of the remaining seeds and spacers. Following the rotation of the end 138 in FIGS. 5 and 6, the stylet 104 is engaged with the housing 106 because knob 124 has engaged thread 148. However, the same rotation that engages the stylet to the housing 106 also frees the needle 102 from the housing by rotating the wing 132b out of engagement with groove 150. The needle 102 can therefore be slid rearward in the axial direction A relative to the housing 106 and the stylet 104. As the needle 102 is withdrawn axially over stylet 104, the remaining seeds and spacers within the needle 102 remain within the path of the withdrawn needle, and are implanted in a line extending axially rearward from the position of the first seed toward the stylet tip 118. When the needle 102 is fully retracted the needle hub 112 contacts the stylet hub 120, and the implantation is complete. The needle assembly 100 is then withdrawn from the patient.

The procedure described above is repeated for each position of the prostate requiring treatment by reinserting the needle through different positions of the template 304 (FIG. 17). Throughout the procedure, the practitioner need only maintain the axial spacer 152 in contact with the template 304 as shown to ensure that the implantation occurs at the desired depth in the target tissue (such as the prostate).

Although the needle assembly 100 was described in association with the optional axial spacer 152, the needle assembly 100 can also be used without the axial spacer 152. For example, some needle racks may not accommodate the needle assembly 100 having the axial spacer 152.

To determine a desired starting position without using the axial spacer 152, a guard placed over the template 314 can be used. The guard is spaced rearwardly from the template at a known distance, and is configured to receive the forward end of the needle hub portion 112. In this way, the needle hub portion 112 can be abutted with the guard to establish a known reference position upon starting the procedure.

Alternative First Embodiment

A needle assembly 600 according to an alternative first embodiment is shown in FIGS. 39A–49. In the alternative first embodiment, elements corresponding to the elements of the first embodiment described above are numbered with the first embodiment reference number plus 500.

In the needle assembly 600, the housing 606 and the needle 602 are shaped to cooperate with an optional, separate element, referred to as a pusher 680, that is used to secure the seeds within the assembly before loading (such as during transport), and to load the seeds into the needle 602. Thereafter, the stylet 604 is used as described above to implant the seeds during a procedure.

In the needle assembly 600, correct positioning of the needle tip 608 at the over-insertion and insertion depths is achieved by abutting or engaging different features of the housing 606 with a stationary object (e.g., the template 304 or a stop, such as the stops described below in connection with FIGS. 27–31 and FIGS. 50–52).

In the needle assembly 600, the needle 602 has an axial rib 647 (see, e.g., FIG. 41) projecting from its outer surface and extending along a portion of its length. The rib 647 prevents the needle 602 from being axially retracted because the rib 647 contacts a collar at the distal end of the housing 606 (unless the rib 647 is rotated relative to the housing 606 into alignment with a gap in the collar, as explained in greater detail below).

The needle assembly 600 is shown with the seeds C provided in a self-contained strand E, which is shown in relation to the pusher 680 in FIG. 39A. The strand E is a series of evenly spaced seeds C that are connected together as a single element by a surrounding shroud of flexible material. In specific embodiments, the shroud extends beyond the last seed on either end by a distance less than the length of one seed. Use of the strand E eliminates the need for spacers D and some of the repeated operations involved in handling multiple seeds. The strand E is implanted with the seeds C contained within it.

The needle assembly 600 can also be used with separate seeds C and interspersed spacers D as described above. Similarly, the needle assembly 100 and the other embodiments described below could be configured for use with strands instead of separate seeds and spacers.

In general, except as described above and in the sections that follow, the construction and operation of the needle assembly 600 is the similar to the construction and operation of the assembly 100. Thus, the needle 602 and the stylet 604 can each selectively engage the housing 606, by rotation, to effect axial displacement of the seeds in a patient.

Construction

Referring to FIGS. 39A and 41, the body 628 of the needle 602 is generally cylindrical over its entire length from the distal needle hub 612 end (i.e., where the needle shaft extends from the body 628) to its proximal end 638, which extends beyond the housing 606. The cylindrical needle body 628 includes a longitudinal groove 636 at the bottom of a longitudinal slot 637 that extends into the body 628 from its proximal end 638 to a point L (FIG. 40) at the origin of the needle shaft near the needle hub portion 612. The groove 636 receives the seeds or seed strand and stylet 604.

The slot 637 is sized to receive a pusher 680, as described below. In the illustrated embodiment, the rib 647 has a circular cross-section and is formed on the outer surface of the body 628 at approximately 150 degrees from the groove 636 (FIG. 42A).

Figure 42A:
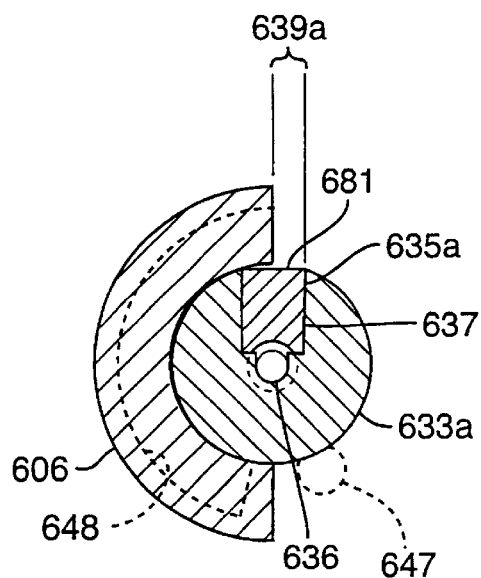
FIGS. 42A and 42B are sectional views of the needle assembly taken along the lines 42A—42A and 42B—42B, respectively, of FIG. 41.

Referring to FIGS. 39A, 41 and 42A, the housing 606 is channel-shaped with a substantially semi-circular cross-section sized to receive the needle 602. The distal end 606a of the housing 606 has a flat face 607 that is brought into contact against a stationary object to space the needle tip 608 at the insertion depth during a procedure. Spaced proximally from the flat face 607, the housing 606 also has a step 609 that can be brought into contact with the stationary object when it is desired to position the needle tip 608 at an over-insertion depth.

Near its distal end 606a, the housing 606 has a distal collar 633a, which extends approximately perpendicular to the housing 606 and has a generally circular periphery with an opening 635a (FIG. 42A). Within the opening 635a, an upper end of the distal collar 633a is separated from the side 606d of the housing 606 by a gap 639a. The distal collar 633a serves as a stop to prevent axial movement of the needle 602 in the insertion direction, but the needle shaft projects through the opening 635a, and the pusher 680 can be slid through the opening 635a (FIG. 43).

Figure 42B:
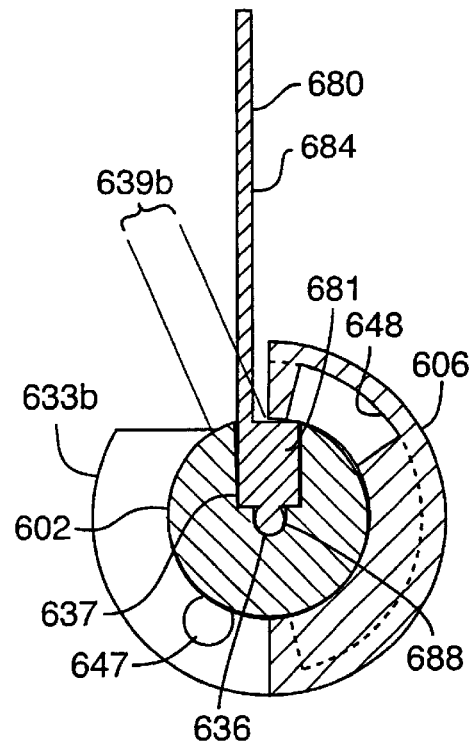
Figure 42C:
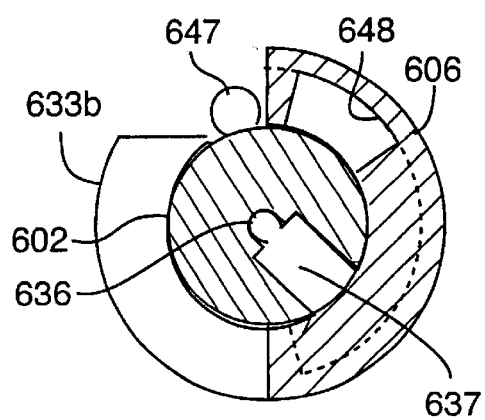

As shown in FIG. 42B, at the proximal end 606b of the housing 606, there is a narrow proximal collar 633b that extends partially across the open top of the housing 606, leaving a gap 639b between the collar 633b and the side 606d of the housing. The proximal collar 633b defines a semi-circular opening at the proximal end 606b, which is slightly larger than the diameter of the needle body 628 to allow the needle 602 to be retracted from the housing 606 when properly aligned.

FIG. 39A shows the needle fully inserted in the housing 606 as shown, with the needle hub end contacting the distal collar 633a. The rib 647 (FIGS. 41 and 42) is positioned such that its proximal end abuts and rotates against the proximal collar 633b, but is restricted from moving axially. With the needle positioned in this fashion, the needle 602 cannot be moved in the axial direction relative to the housing 606 because of the collars 633a, 633b and the rib 637. However, if the needle is rotated to align rib 637 with the second gap 639b (FIG. 42C), the needle 602 can be retracted from the housing 606.

In alternative embodiments, the rib 637 is formed to have a repeating wave pattern and the gap 639b is shaped accordingly to allow the aligned rib to pass through it. In these embodiments, the repeating wave pattern of the rib 639b causes the needle shaft to rotate slightly in an oscillating manner as the needle 602 is withdrawn, which tends to reduce any friction between the needle tip and the surrounding tissue.

Referring to FIG. 45, the stylet 604 has a stylet hub 620 attached to a proximal end of the stylet shaft, and the hub 620 is shaped to slide within the slot 637. In the stylet 604, the stylet/housing engaging feature is a cylindrical projection 624 extending from the stylet hub 620 near its distal end.

Referring to FIG. 41, the housing 606 has a series of evenly spaced, substantially parallel, interrupted or partial inclined threads 648 that define part of a helical path, and are formed in the housing inner surface. The threads 648 are shaped to receive the projection 624 (FIG. 45) when the stylet 604 is rotated into engagement with the housing 606. The projection 624 and the threads 648 may be shaped such that engaging the projection 624 in one of the threads 648 produces an audible "click" or a change in feel as a signal to the practitioner. The threads 648 may be spaced by the distance separating the seeds D in the strand E (e.g., approximately 1 cm), and may be labeled according to the seed count at their respective positions.

In operation, after the stylet 604 is engaged with one of the threads 648, further rotation in the same direction causes the projection 624 to move along the path of the inclined thread 648 with which it is engaged. This movement causes stylet 604 to advance in the axial direction until the projection 624 reaches the end of the selected thread, at which point the rib 637 on the needle 602 has rotated into alignment with the second gap 639b, allowing the needle 602 to be retracted.

As shown in FIG. 39A, the pusher 680 has a body 681, a distal end 682 and a fin-shaped handle 684 extending from a proximal end. The pusher 680 has a length slightly greater than the distance between the first and second collars 633a, 633b. The body 681 has a generally rectangular cross-section sized to slide within the slot 637 (FIGS. 42A and 42B).

As also shown in FIG. 39A, along a bottom surface of the body 681 near the proximal end, the pusher 680 has a rib 688 dimensioned to slide within the groove 636. Spaced from the rib 688 toward the distal end 682, a deformable projection 690 extends from the bottom surface of the body 681. The distance between the projection 690 and the rib 688 is at least as long as the length of the strand E. When the pusher 680 is engaged with the housing 606, the projection 690 extends into the groove 636 and thus prevents seeds from passing through the opening 635a and entering the needle 602. When the pusher 680 is used to load the strand E into the needle 602, forward axial pressure on the pusher deforms projection 690 toward the body 681 to allow the pusher 680 to pass through the opening 635a.

The pusher 680 can be inserted through the first collar 633a and pivoted into the slot 637 to secure the pusher 680 within the housing 606. Referring to FIG. 42A, which shows a cross-section of the needle assembly with the body 681 of the pusher in the slot 637, the opening 635a is shaped to receive the distal end 682 of the pusher 680. The first gap 639a is dimensioned to allow the handle 684 to pass as the pusher 680 is urged toward the distal end. Because the pusher body 681 cannot pass through the first gap 639a, the pusher 680 remains coupled to the housing 606 during this operation.

As shown in FIGS. 42A and 42B, the handle 684 extends from one side of the body 681. The trailing end of handle 684 has two parallel slots 686a, 686b that define a tab 686c between them (FIG. 39A). The tab 686c has a rib 686d extending transverse to the body 681 (FIG. 39B). To lock the coupled pusher 680 in place with the housing 606, the handle is rotated relative to the housing 606 in the direction of arrow M to urge the rib 686d into engagement with a groove 641 (FIG. 43) formed in the side 606c of the housing 606.

Operation

In operation, with the needle in the position shown in FIG. 39A, the strand E is placed within the groove 636.

As shown in FIGS. 40 and 41, the pusher 680 is then inserted into the housing 606 and locked in place to secure the strand E between the rib 688 and projection 690 of the pusher. To insert the pusher 680, the user grasps the handle 684, places the distal end 682 in the opening 635a in the first collar 633a, and pivots the pusher 680 toward the slot 637. Once the pusher 680 is in place within the slot 637, the pusher 680 can be locked by rotating it in the direction of arrow M such that the rib 686d (FIG. 39B) engages the groove 639.

In preparation for a procedure, the pusher 680 is used to urge the strand E into the needle 602, as shown in FIG. 43. First, the pusher 680 is unlocked by rotating it in the opposite direction from the locking direction. The pusher 680 is then moved in the insertion direction, causing the rib 688 to urge the strand E into the needle 602. The projection 690 deforms as it passes through the opening in the first collar. After the strand E is fully inserted within the needle 602, the pusher 680 is retracted (FIG. 44) and removed by reversing the operations by which it was inserted.

As shown in FIG. 45, the stylet 604 is then inserted into the loaded needle 602. As shown in FIG. 46, the stylet 604 is then advanced until the projection 624 is adjacent to one of the threads 648 corresponding to the proper seed count. The stylet 604 is rotated slightly to engage the projection 624 in the thread 648, thus preventing uncontrolled axial movement of the stylet 604 relative to the housing 606 from the slight axial force developed in the succeeding over-insertion step. In this position, the axial position of the needle 602 is also locked relative to the stylet 604 and the housing 606.

FIG. 47 illustrates over-insertion of the needle assembly 600, with the stylet 604 partially engaged as in FIG. 46. The needle tip has been inserted through a desired aperture 312 in the template 304, and the flat front face 607 of the housing 608 brought into contact with a movable arm 454 of a stop 450 (as described in greater detail in association with FIGS. 27–31 and FIGS. 50–52). As shown in FIG. 47, the needle tip position is confirmed by advancing the needle assembly in the insertion direction until the recessed step 609 near the tip of the instrument engages a proximal edge of the arm 454, thus positioning the needle tip at the over-insertion depth.

With the position of the needle tip 608 confirmed, the instrument is retracted and rotated, and the flat face 607 at the tip of the instrument is brought into contact with the arm 454, as shown in FIG. 48. In FIG. 49, the strand E is implanted by first rotating the needle 602 relative to the housing 606, which fully engages the projection 624 of the stylet 604 (FIG. 45) with the adjacent thread 648, and moves the stylet axially as the projection 624 slides along the path of the angled thread. This slight axial movement of the stylet ejects any bone wax plug at the needle tip, and implants the most distal seed just beyond the needle tip. The same rotation also aligns the needle rib 647 (FIG. 42C) with the gap 639b in the proximal collar, such that the needle 602 can be retracted axially from the housing 606 to implant the remainder of the strand E, as shown in FIG. 49. The strand E is implanted by retraction of the needle 602 because the stylet within the needle maintains the strand stationary as the needle is retracted.

Alternative Stylet/Housing Engagement

Figure 20:
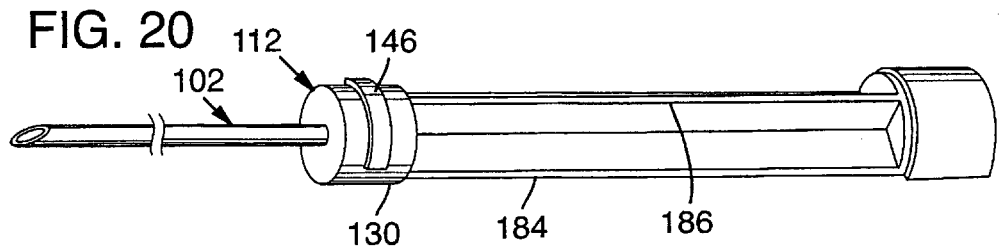
FIG. 20 is a perspective view of an opposite side of the needle hub of FIGS. 18 and 19 showing the axial rib.

As illustrated in FIGS. 19 and 20, the stylet/housing engaging feature 124 may be a thread-shaped groove 180 formed in the outer surface 140 of an alternative stylet hub 120', and the stylet receiving feature 125 in the housing 106 may be a set of thread-shaped ribs 182 extending from the inner surface of the housing 106. The thread-shaped ribs 182 have the same size and position as the set of threads 148 of the first embodiment, but they project outwardly from the inner surface of the housing 106, rather than being recessed into that surface. The thread-shaped groove 180 on the stylet hub 120' is shaped complementary to the thread-shaped ribs 182 such that the thread-shaped groove 180 follows an adjacent one of the thread-shaped ribs when the stylet 104 and the housing 106 are engaged.

In the illustrated embodiment, the stylet hub 120' is formed as a solid member having a wedge-shaped cross section, with bottom surfaces 142a and 142b that are inclined relative to one another. The needle hub 112 has an upper surface portion 184 with surfaces 184a, 184b inclined relative to one another at an angle such that surfaces 184a, 184b are complementary to bottom surfaces 142a, 142b of hub 102'. A longitudinal groove 136 extends through the hub at the intersection of surfaces 184a, 184b, to provide a guide in which hub 112 slides. In addition, as shown in FIG. 20, the bottom face of the needle hub 112 can be provided with a longitudinal rib 186 that extends along the length of angled portion 184, and is complementary in shape to groove 136 such that rib 186 rides in groove 136.

These modifications can provide for smooth operation of the needle assembly 100 because: (1) the wedge-shaped stylet hub 120' easily engages one of the threads 148 or ribs 182, and the stylet hub 120' resists becoming dislodged from the housing 106; and (2) the axial rib 186 stiffens the needle hub 112, thus inhibiting torsional deformation in the needle hub 112 as the needle hub 112 is turned to rotate stylet hub 120'.

Single-use Feature

It is sometimes advantageous to indicate whether the instrument has already been used, or to inhibit additional uses. For example, the instrument may need to be sterilized after use, or discarded if the instrument is disposable. As illustrated in FIGS. 18 and 19, the needle assembly 100 may include a single use feature 187 that prevents the needle assembly 100 from being reused, e.g., as a safety precaution. In a specific implementation, the single use feature 187 includes a spring hook 188 extending from a distal surface of the stylet hub 120 and an aperture (not shown) in the proximal surface of the needle hub portion 112. The spring hook 188 is in a position that it passes through the aperture just before needle hub portion 112 abuts the stylet hub when the needle 102 is slid rearwardly relative to the stylet 104. When spring hook 188 passes through the aperture, the spring hook 188 engages the needle hub portion 112, thus inhibiting disengagement of the needle 102 and the stylet 104 until the spring hook 188 is manually removed.

Alternative Seed Loader

An alternative seed loader 700 is shown in FIG. 53. The seed loader 700 has a flared end 702, and a tubular housing 704 with a closed distal end. The housing 704 is shown loaded with seeds C and spacers D, and is sized to be inserted over a needle shaft 708 having a beveled tip 710. Thus, the seed loader 700 allows the seeds C and the spacers D to be loaded into the needle shaft 708 through its tip 710, by inserting needle shaft 708 into seed loader 700 until its tip 710 is fully advanced. As the needle is inserted into the seed loader 700, the seeds and spacers are moved into the needle shaft.

The housing 704 may be made from a transparent material to allow easy verification of the seed count.

Spring-Loaded Needle Hub

A needle assembly of the general type described above, with the added feature of a spring-activated automatically retracting needle, is shown schematically in FIG. 54. In the needle assembly 800 of FIG. 54, when a needle 802 is disengaged from a housing 806, a spring 803 urges the needle 802 in the retraction direction N.

FIG. 54 shows the spring 803 in its compressed state with the needle 802 engaged with the housing 806. In this state, the needle 802 cannot move axially with respect to the housing 806. Specifically, the spring 803 is positioned within the housing between its distal end and a distal end 805 of the needle body portion.

By rotating the needle 802 in a direction P, the needle 802 will become disengaged from the housing 806 (i.e., free to move axially relative to the housing 806), and the spring 803 will urge the needle 802 in the direction N, thus serving to automatically retract it.

The needle assembly 800 facilitates seed implantation because the needle need not be retracted manually. Instead, while holding the housing 806, the practitioner simply turns a proximal end 807 of the needle 802 to rotate the needle 802 out of engagement with the housing 806, and continues to hold the housing 806 while the needle retracts automatically.

Instead of the compression spring 803, it is also possible to achieve the same result by configuring the assembly 800 with a tension spring. In addition, the spring action may be suitably damped to provide acceptable kinesthesia and control during operation of the instrument.

Second Embodiment

FIGS. 10–16 illustrate a needle assembly 200 according to another embodiment, in which each of the needle and stylet are separately selectively secured or fixed to the housing to allow independent selective movement of the needle and stylet by disengagement from the housing. In this embodiment, elements corresponding to elements of the first embodiment described above are numbered with the first embodiment reference number plus 100. The illustrated construction of the needle assembly 200 minimizes the risk of unintentionally moving the needle 202 and/or the stylet 204 in the axial direction A during a brachytherapy procedure. In general, the needle 202 and the stylet 204 are each independently slidable in the axial direction relative to the housing 206 by direct manipulation of respective knobs projecting outside the housing 206.

As illustrated in FIG. 10, the housing 206 of the needle assembly 200 is generally tubular, with a spread leaf-type spring spacer 209 extending from a forward end 211, and an open rearward end 213. A longitudinal slot extends through an upper surface of the housing 206, from an anterior tip of the instrument to its rearward end 213, and the slot is defined by opposing side edges 207a and 207b. The side edge 207a has a first repeating pattern of teeth, and the side edge 207b has a second, different repeating pattern of teeth.

Figure 16:
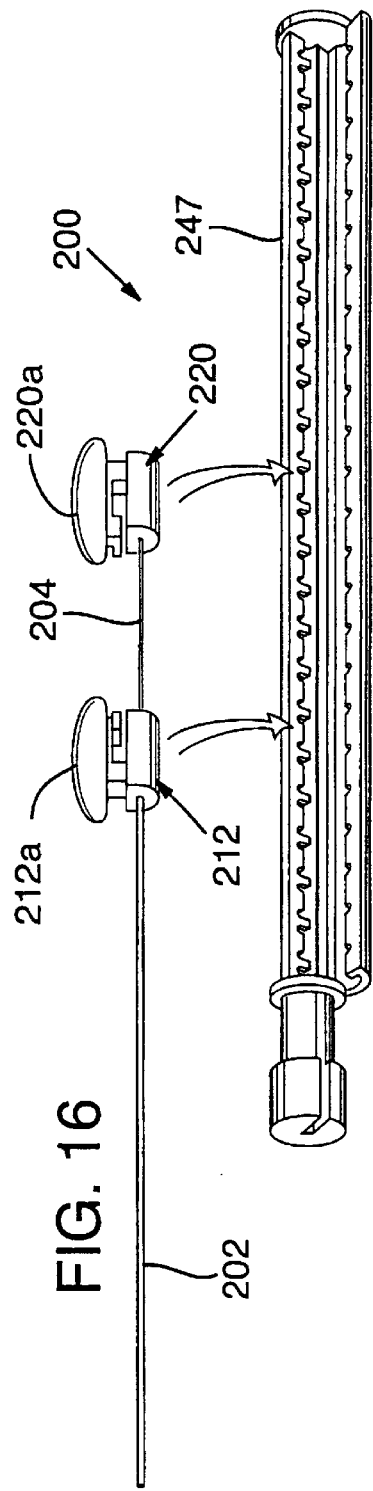
FIG. 16 is a perspective view of a needle assembly having a hinged housing.

The stylet 204 slides within the needle 202, similar to the first embodiment, as most clearly illustrated in FIG. 16. At the proximal end of the needle 202 is a needle hub 212 which includes a knob 212a, and at the proximal end of the stylet 204 is a stylet hub 220 which includes a knob 220a. The knobs 212a and 220a project outwardly from the slot 207 beyond the housing 206 (FIG. 11). As illustrated most clearly in FIG. 16, the stylet hub 220 and the needle hub 212 are substantially identical, but turned 180 degrees to one another. As illustrated in FIGS. 12 and 13, the needle hub 212 has a housing engaging portion 212b and the stylet hub 220 has a housing engaging portion 220b.

In the illustrated implementation, the knobs 212a, 220a each include a hub member 225 (FIG. 12) that fits around the respective needle 212 or stylet 204, an arm 227 that connects the hub member 225 to the knob, and an L-shaped trigger member 229. The trigger member 229 depends from the knob to a depth J and has a laterally projecting free end with an engaging tip 231 at that depth. The arm 227 is positioned at a distal end of the needle hub 212, whereas the arm is positioned at the proximal end of the stylet hub 220. The arm 227 is resilient, such that the knob portion can be depressed to disengage the engaging tip 231 from teeth along either side of the slot.

As seen from an end of the hub in FIG. 13, the hub member 225 has a rounded bottom surface such that it can freely slide within the housing 206. The arm 227 and an upper part of the trigger member 229 are dimensioned to slide within the slot 207, but the engaging tip 231 projects transverse to the axial path of movement of the needle and stylet to engage one of the side edges 207a, 207b. The stylet hub 220 engages side 207a while the needle hub 212 engages side 207b. The side edge 207a has a first repeating pattern, while side edge 207b has a different repeating pattern.

The first repeating pattern of the side edge 207a has spaced teeth which allow the stylet 204 to slide axially for a predetermined distance (for example about 0.8 cm to about 1 cm) within the particular interval in which the stylet 204 is retained. The engagement between the engaging portion 220b and the side edge 207a prevents the stylet 204 from sliding forward into the forwardly adjacent intervals or rearwardly into the rearwardly adjacent intervals. In contrast, the repeating pattern of edge 207b does not have spaced teeth, but instead provides a series of discrete indentations which do not permit axial movement of the needle hub when it is engaged with one of the discrete indentations.

Figure 10A:
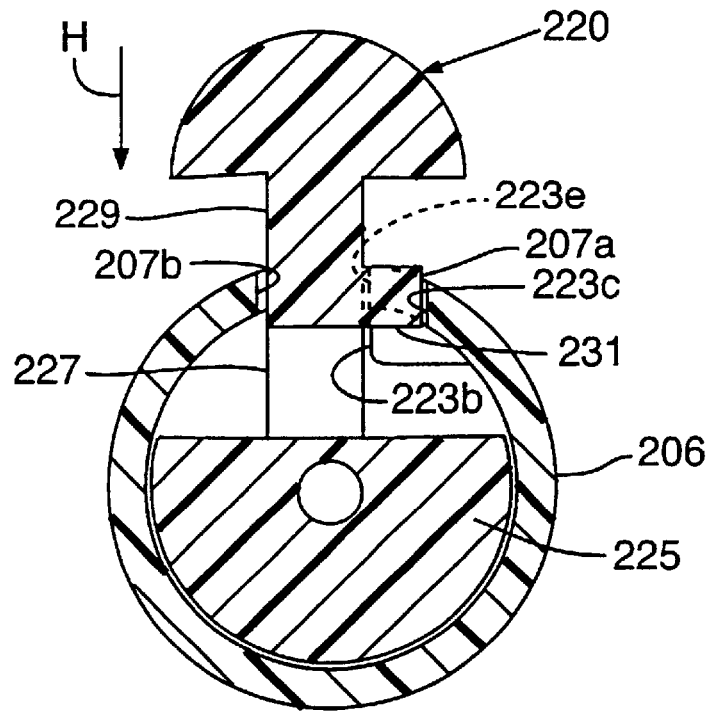
FIG. 10A is a sectional view of the needle assembly of FIG. 10 viewed in the direction of the line 10A—10A of FIG. 10.

As illustrated in FIG. 10, an exemplary interval 223 of the first repeating pattern is the space in the axial direction A between two adjacent inwardly projecting tabs 223a, 223b. Within the interval 223 are arranged a rearward slot 223c adjacent the tab 223a, a forward slot 223d adjacent the tab 223b, and an intermediate portion 223e between the slots 223c, 223d. The slots 223c, 223d are each dimensioned to receive the engaging tip 231 of the stylet hub 220. FIG. 10A shows an end view of the stylet hub 220 in relation to an adjacent interval of the first repeating pattern of the housing, which has been labeled consistent with the exemplary interval 223.

To move the stylet hub forward in the axial direction A when the stylet hub is engaged in the rearward slot 223c, the stylet hub 220 must be depressed in the direction H (FIG. 10A) such that the engaging tip 231 is disengaged from the rearward slot 223c, slid forward beneath the intermediate portion 223e, and then released to allow the engaging tip 231 to engage the forward slot 223d. The forward tab 223b prevents further forward movement of the stylet hub 204 (without disengaging the stylet hub 220 from the housing 206). The positioning and movement of the stylet hub 220 during operation of the needle assembly 200 are described below in greater detail.

The engaging portion 212b of the needle hub 212 engages the opposite side edge 207b having the second repeating pattern. The second repeating pattern allows the needle hub 212 to be indexed in the axial direction by a regular interval (preferably about 1 cm).

Figure 10B:
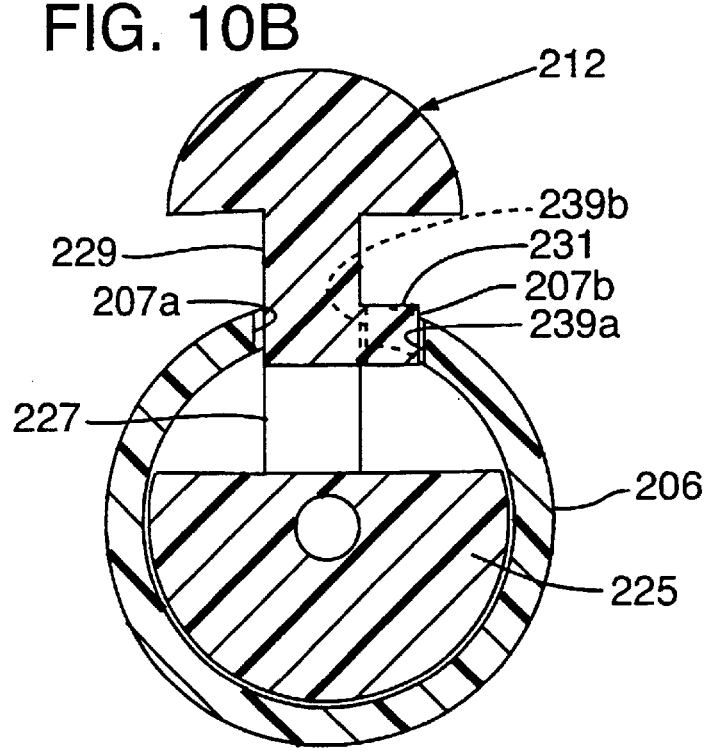
FIG. 10B is a sectional view of the needle assembly of FIG. 10 viewed in the direction of the line 10B—10B of FIG. 10.

As illustrated in FIG. 10, within an exemplary interval 239 of the second repeating pattern are arranged a slot 239a and a straight portion 239b positioned adjacent and rearwardly of the slot 239a. The slot 239a is dimensioned to receive the engaging tip 231 of the needle hub 212. The straight portion 239b is shaped to prevent the needle hub 212 from moving in the axial direction unless it is depressed to pass beneath the straight portion 239a. FIG. 10B shows an end view of the needle hub 212 in relation to an adjacent interval of the second repeating pattern of the housing, which has been labeled consistent with the exemplary interval 239.

Alternative Knob Portion Shapes

The knobs 212a and 220a are sized and shaped for easy manual digital manipulation. The needle and stylet hubs preferably have the same shape for ease of manufacture, but two distinctly shaped knob portions may also be used. Alternative shapes for the knob portions are shown in (1) FIGS. 10, 11, 14 and 15, (2) FIGS. 12 and 13, and (3) FIG. 16. Other alternative shapes are also possible.

Spring Spacer

The spring spacer 209 (FIG. 10) serves to space the needle assembly from the template 304, similar to the spacer 152 in the first embodiment. In addition, the spread leaf design of the spring spacer 209 can be flexed to allow the needle assembly 200 to be urged forward slightly to verify the position of the needle tip on the ultrasound image, similar to the spring 164 of the first embodiment. Alternatively, the needle assembly 200 could be modified to include the spacer 154 of the first embodiment.

Operation

In operation of the needle assembly 200, the needle 202 is assembled with the housing 206 by fixing the needle hub 212 at a predetermined position on the side edge 207b for the correct needle insertion depth. The needle 202 is loaded with seeds and spacers, and the stylet 204 is then inserted into the needle 202 so that the tip of the stylet abuts the last seed or spacer.

The stylet hub 220 is then assembled with the housing 206 by fixing the stylet hub 220 at a predetermined position on the side edge 207a. In particular, the stylet 204 is first positioned axially at the desired interval with the engaging tab 231 of the stylet hub 220 positioned outside of the slot 207. The stylet 204 is then fully seated in the housing 206 at the desired interval by urging the stylet hub knob 220a inwardly so that the engaging tip 231 is pushed through the slot 207 and into engagement with the rearward slot 223c in the interval. Thus, once the stylet is seated within a particular interval in such a manner, the stylet 204 is restricted to moving axially within the range defined by the tabs 223a, 223d. With the stylet 204 in position, the needle tip position can be confirmed as described above.

During implantation, the stylet hub 220 is slid forwardly to deposit the first seed just forward of the needle tip. Specifically, the stylet hub 220 is depressed in the direction H (FIG. 10A) to disengage the engaging tip 231 from the rearward slot 223c, the stylet hub 220 is slid forward with the member 231 sliding beneath the intermediate portion 223e, and, by releasing the pressure on the stylet hub knob 220a, the engaging tip 231 is engaged in the forward slot 223d. As illustrated, even when the stylet hub knob 220a is depressed, the stylet hub 220 cannot be slid past the tabs 223a.

Thereafter, the needle 202 is slid rearwardly over the stationary stylet to unsheath and deposit the seeds and spacers along the path of the needle. The needle 202 is slid rearwardly from its position in the initial interval by (1) depressing the needle hub 212 inwardly to disengage the engaging tip 231 from the slot 239a and (2) sliding the needle 202 rearwardly through adjacent intervals while maintaining the pressure on the needle hub 212 to keep the engaging tip 231 disengaged. Preferably, the knob portions 212a and 220a are sized such that the knob 212a of the needle hub just contacts the knob portion 220a of the stylet hub 220 when the implantation is complete.

Alternative Spacer/Spring Design

Figure 14:
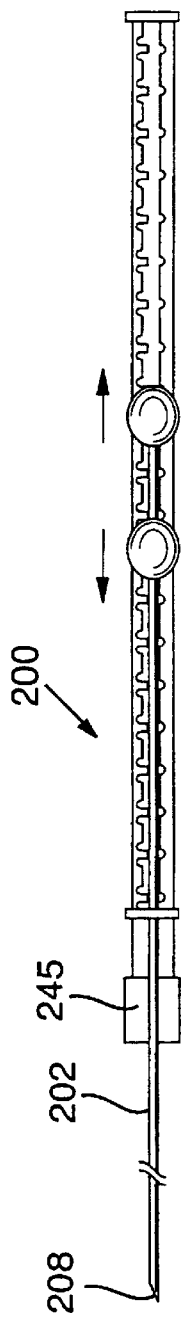
FIGS. 14 and 15 are top and side views, respectively, of a needle assembly according to the second embodiment with an alternative spring spacer.
Figure 15:
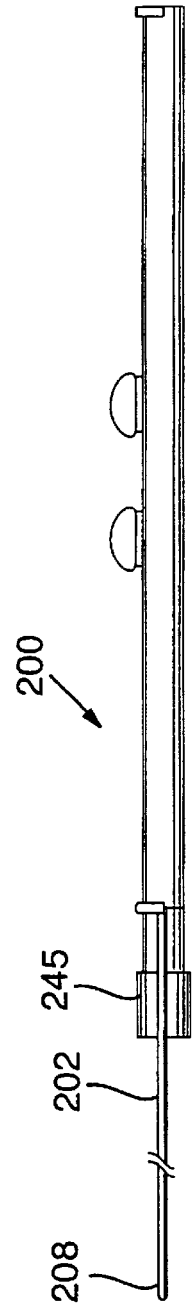

As illustrated in FIGS. 14 and 15, the needle assembly 200 may be configured with a cylindrical spring spacer 245 instead of the spread leaf spring spacer 209 shown in FIG. 10. The cylindrical spring spacer 245 is axially aligned with the needle 202. The cylindrical spring spacer 245 is configured to resiliently axially compress. During a procedure, the cylindrical spring spacer 245 is positioned in contact with a flat surface (e.g., the template 304), and the needle assembly 200 can be urged forward slightly to verify the position of the needle tip 208 as cylindrical spring spacer 245 compresses. Subsequent removal of the pressure allows the spring spacer 245 to expand to its original dimensions. Although the spring spacer is described in connection with the needle assembly 200, it can also be used in place of the spacer 152 for the needle assembly 100 of the first embodiment.

Alternative Housing Design

As illustrated in FIG. 16, the housing 247 of needle assembly 200 may have a hinged portion that can be opened for loading and closed for operation. The housing 247 is useful with a separately stored and/or preloaded assembly of the needle 202 and the stylet 204. This feature may be advantageous when the instrument is placed in a needle rack that will not accommodate the housing 206.

The components of the needle assembly may be constructed of any suitable materials. For example, the needle and the stylet may be constructed of a surgical-grade steel, as would be known to those of ordinary skill in the art. The housing, needle hub, stylet hub and spacers may be constructed of any suitable material, including, e.g., a plastic material. The cylindrical spring spacer may also be constructed of a suitable grade of surgical rubber or other similar material.

Alternative Needle Fixation

In the embodiments described above, the stylet is advanced in the axial direction to implant the first seed at a predetermined position, as well as to generate a force sufficient to eject any bone wax plug present at the needle tip. The bone wax plug is used to prevent the seeds from inadvertently falling out of the needle or being implanted improperly. Since the plug seals the needle, it requires a greater force to eject the plug than to move the seeds, which slide within the needle shaft.

In embodiments where the plug is easier to eject or is not used, the stylet need not be advanced relative to the needle and the housing. In these embodiments, the position of the stylet can be fixed relative to the housing throughout the implantation procedure. The stylet can also be formed as part of the housing (if the seeds are loaded through the needle tip).

Figure 55:
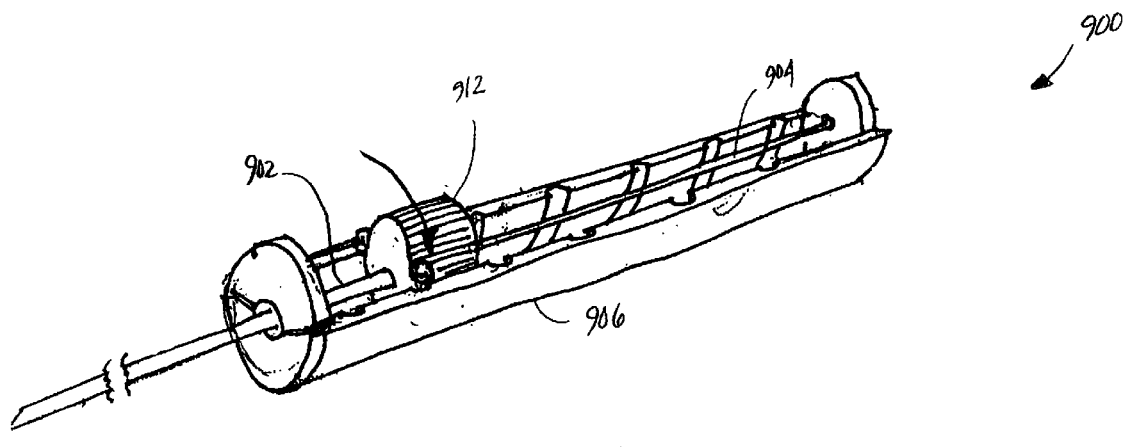
FIG. 55 is a schematic top perspective view of another embodiment in which the needle is latched and unlatched from a housing by rotating the needle by manipulating a needle hub that has knobs which interact with guide members on the housing to controllably retract the needle.

One such embodiment is shown in FIG. 55. In an assembly 900, the stylet 904 is axially fixed relative to the housing 906, and the needle 902 is rotated to retract it in the axial direction relative to the stylet 904 and the housing 906. The needle 902 is initially in an axially locked condition, and rotating the needle hub 912 to a predetermined position frees the needle for retraction.

Figure 56:
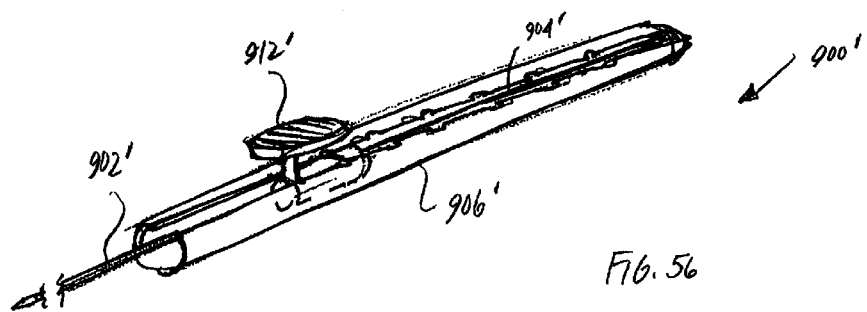
FIG. 56 is a schematic top perspective view of another embodiment in which only the needle is fixed to the housing to inhibit axial movement of the needle.

FIG. 56 shows an assembly 900', which is similar to the assembly 900, except the needle 902' has an exposed needle hub knob 912' similar to the second embodiment, and the needle 902' is selectively moved relative to the stationary housing 906' and stylet 904' by depressing the knob 912'.

Third Embodiment

According to a third embodiment, a stop that prevents the needle from being inserted beyond a desired position is provided. The stop provides a surface which the needle (or needle assembly) contacts to prevent further advancement of the needle/needle assembly in the insertion direction. Optionally, the needle/needle assembly may also be engaged with the stop to stabilize the needle tip and to avoid any inadvertent withdrawal of the needle. According to specific implementations, the stop is removably attached to the ultrasound probe and/or its carriage. Thus, the stop may move with the ultrasound probe/carriage as the probe is initially inserted into the patient.

Figure 21:
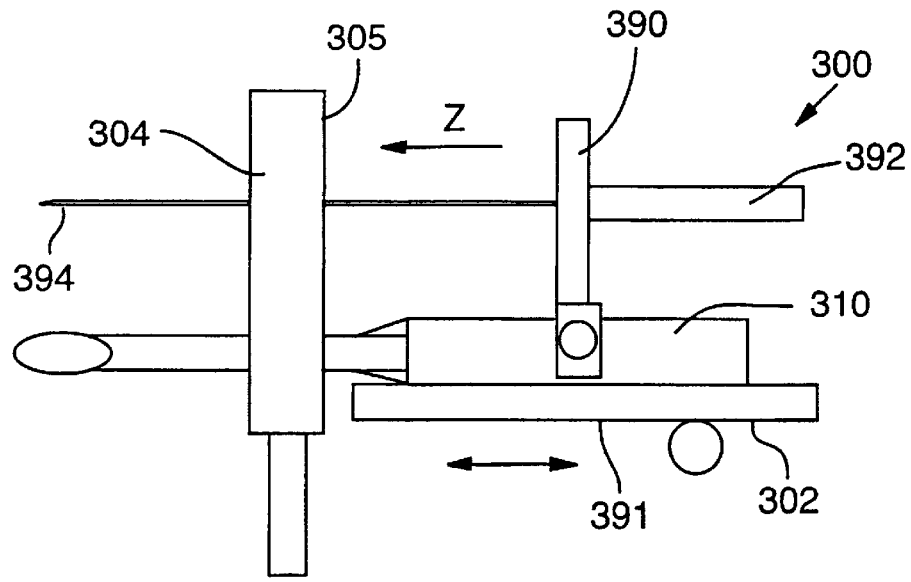
FIG. 21 is a schematic side view of a brachytherapy assembly showing a stop that prevents further insertion of a needle beyond a predetermined point.

Referring to FIG. 21, a schematic side view of the conventional brachytherapy system 300, which is generally in accordance with FIG. 17, is shown as modified to include a stop 390. As shown in FIG. 21, the stop 390 is removably attached to the ultrasound probe 310 by a connector 391 at a point spaced from the proximal face 305 of the template 304. The position at which the stop 390 is attached to the ultrasound probe is selected such that a tip 394 of a needle 392 would be positioned at a desired position when the tip 394 is fully advanced in the z direction, for example when an enlarged handle or the needle 392 contacts the stop 390 as shown.

The stop 390 can be configured for use with a conventional needle, any of the needle assemblies described above, or any similar brachytherapy needle design.

Stop Plate

One particular example of a stop is a stop plate 400 shown in FIGS. 22–24.

The stop plate 400 has a generally rectangular, plate-like housing 402 with an upper end 404 and a lower end 406. The housing 402 has a thickness T between its proximal face 403a and its distal face 403b. Adjacent its lower end 406, the housing 402 also has an attachment portion 410 by which the stop plate 400 can be attached to the ultrasound probe 310, its carriage, or other suitable object.

A plurality of substantially parallel slots 408 extend partially through the housing 402 from openings in the upper end 404 to closed ends within the housing 402. As shown in FIG. 22, the slots 408 may be substantially parallel to sides 409a, 409b of the housing 402. The slots 408 extend through the entire thickness T of the housing 402, and are sized to receive a needle shaft, for example having a width slightly greater than a needle shaft but less than a width of the enlarged handle of the needle assembly.

In use, a practitioner aligns the needle shaft with the open upper end of an appropriate one of the slots 408, and then moves the needle downwardly in a direction K (FIG. 24) into the slot to a desired position. As shown, upper edges 411 of the slots 408 may be chamfered to widen the open end of each slot and facilitate sliding the needle shaft into and along one of the slots 408. Along the length of the slots 408, optional needle engagement recesses 412 are formed in the distal side 403b of the housing 402. The recesses 412 are formed at any desired interval, e.g., to correspond with the aperture spacing of the template. In the illustrated embodiment, the needle engagement recesses 412 are keyhole shaped notches 414 extending from the distal side 403b partially through the thickness T to a depth d of the stop plate 400.

As shown in FIGS. 25 and 26, an exemplary needle assembly 416 has a handle 417 with an enlarged diameter, a needle 418 with a shaft 420 projecting from the handle 417, and a tab 422 projecting axially from the shaft 420 at an intermediate point along its length. As shown in FIG. 24, after the needle assembly 416 is positioned within one of the slots 408 as described above, the needle assembly 416 can be aligned with an adjacent one of the needle engagement recesses 412 and rotated in a direction F (which may be clockwise as shown) to engage the tab 424 on the needle 418 with the needle engagement recess 412. Thereafter, the needle 416 and/or stylet within the needle can be manipulated as required while the needle remains secured to the stop plate 400.

In the illustrated implementation, the attachment portion 410 comprises a curved cut-out 427 that is sized, e.g., to fit over the ultrasound probe 310. In the illustrated implementation, the cut-out 427 is slightly greater than semi-circular in shape and area. A curved slot 428 that opens at the lower end 406 of the housing 402 is formed at a position spaced apart from and approximately parallel to the cut-out 427, thus defining a clamp member 429. The curved slot 428 has a terminal aperture 430. An aperture 432 sized to receive a thumb screw 434 is formed in a side 409b of the housing 402. The thumb screw 434 has a tip 436 that bears against the free end of the clamp member 429 to urge it against, e.g., the ultrasound probe 310, at any desired position.

In particular embodiments, the stop plate 400 may be formed of plastic, and may be formed as a single piece or from two mating halves. The thickness T of the stop plate 400 may be any suitable dimension, but in specific embodiments is sized on the order of the thickness of the template 305 to assist in preventing bending of the needle.

In use, the stop plate 400 is secured to probe 310 by placing the housing or the probe in cut-out 427, and tightening screw 434 to force clamp member 429 against the probe. A distal tip of needle 418 is moved down into a selected slot 408, by grasping enlarged handle 417 to manipulate the needle assembly 416. When the needle has reached a desired position in slot 408, the needle assembly 416 is advanced axially to introduce the needle into the treated area to a desired position, at which point the enlarged handle 416 abuts against proximal face 403a of stop plate 400 to halt the axial advance of the needle. Needle assembly 416 is then rotated to lock tab 424 in a complementary recess 412, which stabilizes the needle assembly. As previously described, a stylet (not shown) may then be introduced into and through the needle assembly 416 to push seeds out of the assembly and deliver them to a desired position in the treated area.

Low Profile Stop

For some applications, the stop plate 400 may interfere with the practitioner's ability to manipulate the needle assembly and/or to view the area of interest. For such applications, a low profile stop that would still serve to stop the needle from being inserted beyond a desired position, but could be reconfigured to avoid interference, would be advantageous.

Figure 27:
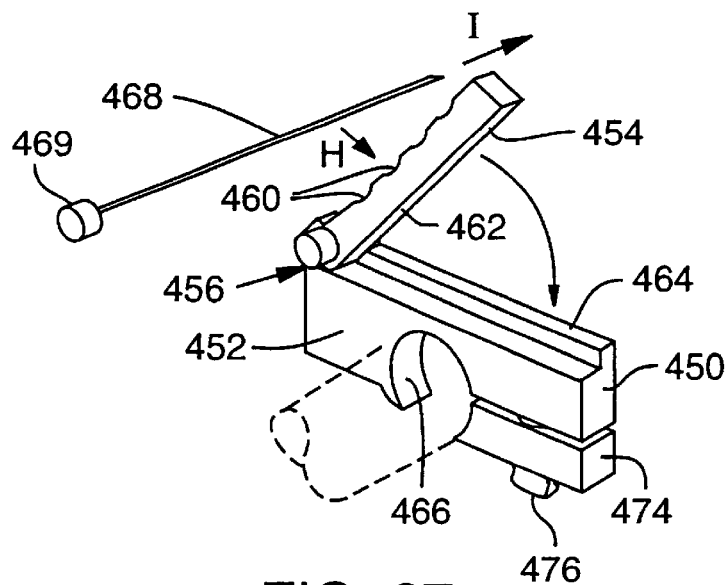
FIG. 27 is a schematic perspective view of a low profile stop having a hinged arm that is pivotable through a range of positions to provide a needle stopping surface and to prevent obstruction.

According to one specific implementation, as shown in FIGS. 27–31, a low profile stop 450 has a base 452 with an arm 454 that is pivotably connected to the base 452 by a hinge 456. Referring to FIG. 27, a first side 458 of the arm 454, which has needle contact features 460: (1) guides a needle 468 as it is being inserted in the direction I; (2) stops the needle from further insertion at a desired point (i.e., by contact between a needle hub 469 and the first side 458); and (3) optionally, engages the needle 468 when it reaches the desired point (with, e.g., needle engagement recesses (not shown) similar to the needle engagement recesses 412 described above).

The arm 454 is sized such that at least one of the needle contact features 460 can be aligned with a desired point of insertion (e.g., either directly on the patient or on the template 304) by pivoting the arm 454 over its range of travel. When the needle contact features 460 are not needed, the arm 454 can be pivoted, e.g., to its fully erect position or such that a second side 462 of the arm 454 rests against an upper side 464 of the base 452.

Optionally, the arm 454 may be biased by a spring (not shown) that urges the arm toward one end of its travel. For example, the spring may be configured such that the arm 454 provides slight resistance against the needle 468 when the arm 454 is in the position shown in FIG. 27.

Figure 29:
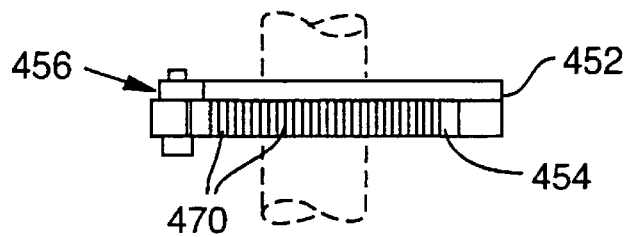
FIGS. 28, 29 and 30 are proximal side, top and right side views, respectively, of the low profile stop of FIG. 27.
Figure 28:
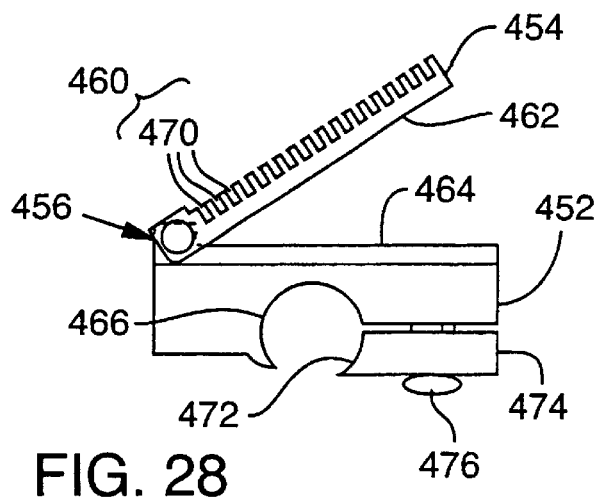
Figure 30:
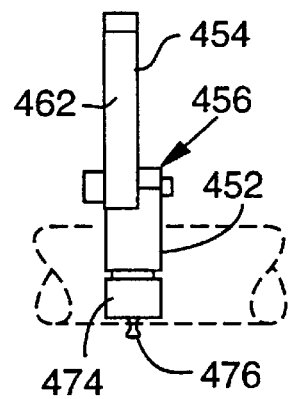
Figure 31:
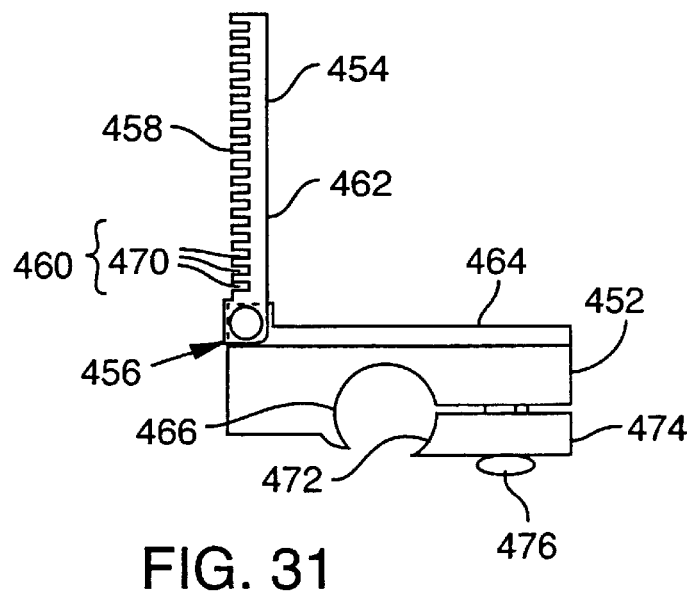
FIG. 31 is an additional proximal side view of the low profile stop, which is similar to FIG. 28, but shows the arm in an erect position.

In the specific embodiment shown in FIGS. 29–31, the needle contact features 460 are slots 470. A desired one of the slots 470 is selected and the needle 468 is inserted into the slot before the needle is moved axially in the insertion direction I. As the needle is moved in the insertion direction, a hub portion 469 of the needle 468 contacts the arm 454 to prevent further insertion of the needle 468.

The arm 454 may be fitted with a spring (not shown) or constructed to be naturally sprung, such that the arm 454 returns to a biased position when not in use (e.g., a fully erect position as shown in FIG. 31). Also, the spring provides a slight resistance when the needle is engaged with the arm 454 and the arm 454 is moved away from the biased position, such that the arm 454 tends to remain in contact with the needle during its insertion. The arm 454 may also have a catch (not shown) to maintain the arm 454 at any desired inclination relative to the base 452.

The base 452 has an attachment portion 466 that allows the stop 450 to be positioned on the ultrasound probe 302 or its carriage, similar to the stop plate 400. The attachment portion includes a cut-out 472, a clamp block 474 and a thumb screw 476 extending through the clamp block and threadedly received in the base 452. By tightening the thumb screw 476, the clamp block 474 bears against the ultrasound probe 302 or other object, and the stop 450 is held in place at any desired position.

Figure 50:
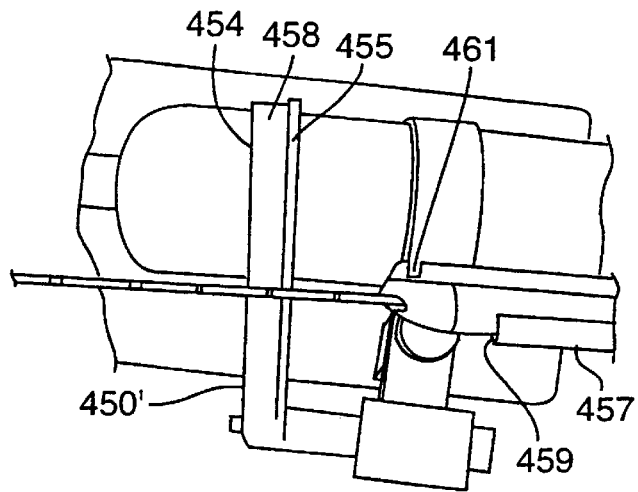
FIG. 50 is a side view of a modified low profile stop similar to the stop of FIGS. 27–31 shown with a needle being advanced toward the modified stop.
Figure 51:
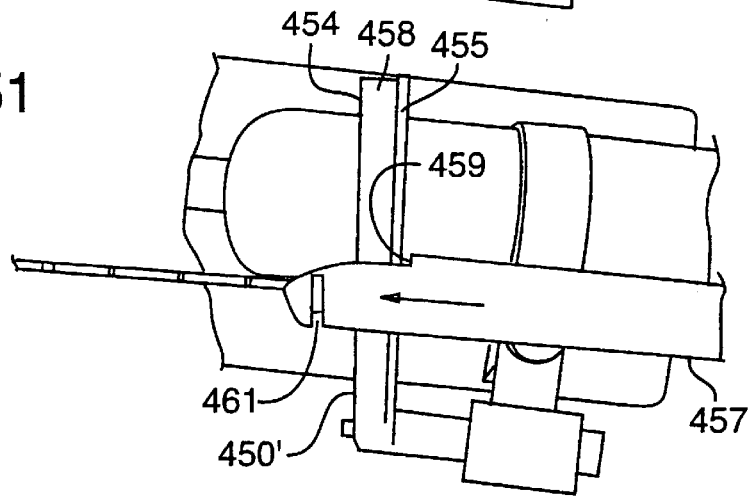
FIG. 51 is a side view similar to FIG. 50, except showing an over-insertion depth step formed on needle coming into contact with the modified stop.
Figure 52:
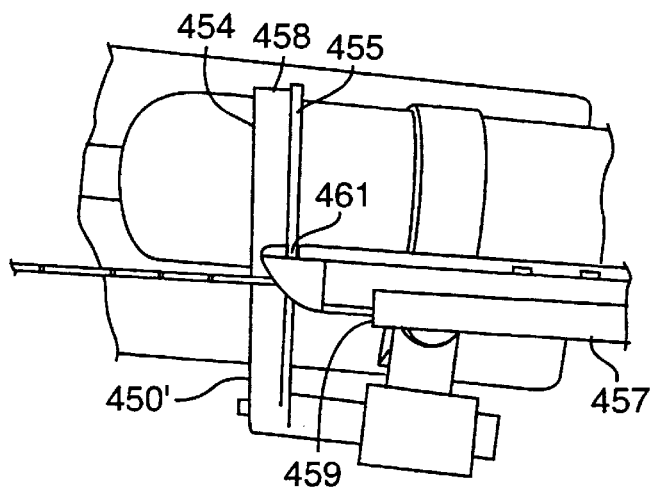
FIG. 52 is a side view similar to FIG. 51, except showing that the needle has been retracted and rotated to engage an insertion depth groove with the rib on the modified stop.

FIGS. 50–52 show a modified stop 450' in which the first side 458 of the arm 454 has a flat surface (instead of the slots 470) with a single rib 455 extending along its proximal edge. As shown in FIG. 50, a needle 457 (or housing of a needle assembly) is formed with a step 459 to position the needle tip at the predetermined over-insertion depth, and a groove 461 to engage with the rib 455 to position the needle tip at the predetermined insertion depth.

In operation, as shown in FIG. 51, the needle 457 is advanced in insertion direction until the step 459 contacts the proximal edge of the arm 454, thus establishing that the needle tip is at the over-insertion depth. With the needle position confirmed, the needle 457 is then retracted and rotated to allow the groove 461 to be engaged with the rib 455, thus establishing the insertion depth, as shown in FIG. 52.

Fourth Embodiment

According to a fourth embodiment, a guide in the form of a movable plate continues to support and guide the needle tip (i.e., the free end of the needle) after the needle tip passes through the template or stop. The movable plate is movably coupled to the template or stop, and has a matrix of apertures corresponding to those of the template or stop. The movable plate is initially positioned adjacent a distal surface of the template or stop. As the needle tip passes through the template or stop and begins exiting its distal side, the needle tip contacts the movable plate and urges it in the insertion direction. The apertures in the movable plate may be sized slightly smaller than the needle shaft (over a portion thereof or their entire depth) such that only the needle tip is received therein initially, and additional force is required to urge the needle shaft through the movable plate, e.g., when the movable plate reaches the end of its travel.

Movable Plate

FIGS. 32A, 32B and 33–37 show a specific implementation of a movable plate assembly 490 in which a movable plate 492 is adapted for use with a conventional template 494 (similar to the template 304 of FIGS. 17 and 21). FIGS. 32A and 32B show use of the movable plate assembly 490 with a conventional needle 568, but the various needle assemblies described above could also be used. The movable plate assembly 490 could also be used in conjunction with other components, e.g., the stop plate 400 or the stop 450.

As shown in FIGS. 34–36, the movable plate assembly 490 includes the movable plate 492 that is movably coupled to the template 494 by a frame of rails 496. As shown in FIG. 34, the rails 496 allow the movable plate 492 to slide toward and away from the template 494 along a direction H. The rails 496 are configured to keep the movable plate 492 substantially parallel to the template 494.

The template 494 has a housing 497 with a proximal surface 498, an opposing distal surface 500 and sides 502a, 502b. The movable plate 492 has a proximal surface 504 and an opposing distal surface 506. As shown in FIG. 35, the distal surface 500 of the template 494 faces the proximal surface 504 of the movable plate 492.

The movable plate 492 has a matrix of apertures 503 arranged to correspond to the matrix of apertures in the template 494. Because of the additional guidance provided by the movable plate 492, the apertures in the template 494 may be sized slightly larger than the needle shaft to facilitate insertion of the needle into one of these apertures.

In particular embodiments, the apertures 503 in the movable plate 492 can be sized at least as large as a tip 570 of the needle 568, but smaller than a shaft of the needle 568. As a result, contacting the movable plate 492 with the needle 568 (with the needle tip 570 received in one of the apertures 503 as shown in FIG. 37) will tend to move the movable plate 492 away from the template 494. When the movable plate 492 reaches its fully extended position (FIG. 32B), further movement of the movable plate 492 in the insertion direction I is halted by stops 505. In the illustrated embodiment, the stops 505 are tabs that contact the proximal surface 498 when the movable plate reaches the end of its travel, as best shown in FIG. 34. Thereafter, additional force on the needle applied in the insertion direction I will urge the needle through the aperture 503, with the movable plate 492 remaining stationary. The complete insertion of the needle through the template 494 may cause a slight but visible deformation of the aperture, thus providing the practitioner with an indication of which apertures have been used when the needle is withdrawn.

FIG. 37 shows a magnified section view of one of the apertures 503 with the needle 570 partially inserted therein. In the specific embodiment shown, the aperture 503 has a reduced diameter portion of a diameter $D_1$ adjacent the distal surface 506 of the movable plate 492, with the remaining portion of the aperture 503 having a larger diameter. The diameter $D_1$ of the reduced diameter portion accommodates the needle tip 570, but is smaller than a diameter $D_2$ of the needle shaft 572.

The template 494 has an attachment portion 506, which includes a cutout 508, a curved slot 510, a clamp member 511 and a thumb screw 512. The adjustment and operation of the attachment portion 506 is the same as the attachment portion 410 described above in connection with FIG. 22.

Single Use Apertures

As described above, the apertures 503 are sized slightly smaller than the apertures in the template such that slight deformation of the movable plate 492 is required to fully insert the needle through the apertures 503. After the needle is fully inserted through one of the apertures, the used aperture has an enlarged appearance, which may provide a visual indication to the practitioner that the particular aperture has been used, e.g., that the brachytherapy procedure for a position corresponding to that aperture has been completed.

Figure 38:
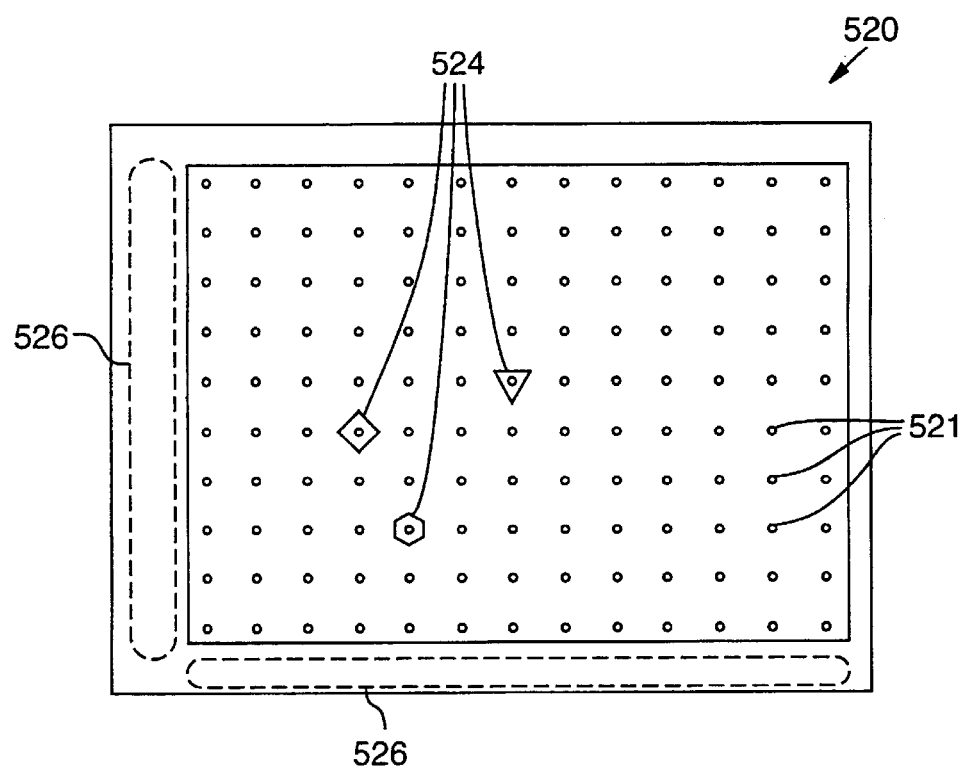
FIG. 38 is a plan view of an overlay with informational symbols suitable for mounting to a template or a stop.

In the same way, an overlay 520 made of transparent plastic or other similar material, as shown in FIG. 38, can be positioned in registration with the apertures in a template and/or a stop plate. The overlay 520 can be attached with an adhesive or by static attraction.

At locations on the overlay 520 corresponding to the apertures 503, the overlay 520 can have symbols or undersized apertures 521. When a needle is inserted through the overlay 520, a pierced aperture 524 is formed at that location in the overlay 520. The pierced aperture 524 has a different appearance, and thus provides a visual indication that the corresponding aperture in the template or stop has been used.

As shown in FIG. 38, the overlay may include various symbols 522 to convey information to the practitioner, e.g., different insertion distances corresponding to different apertures, different seed counts, etc. Also, the overlay 520 can be provided with legends 526, e.g., to indicate the position of any of the apertures, if desired.

Having illustrated and described the principles of our invention with reference to several particular embodiments, it should be apparent to those of ordinary skill in the art that the invention may be modified in arrangement and detail without departing from such principles.

What is claimed is:

1. A brachytherapy device, comprising:
   an elongated needle having a sharp end for insertion into target tissue;
   an elongated stylet which can slide through the needle; and
   a housing that selectively engages the needle and stylet to selectively fix the needle and stylet against axial movement, while allowing the needle to selectively move axially relative to the stylet when the stylet is fixed against axial movement, and allowing the stylet to selectively move axially relative to the needle when the needle is fixed against axial movement.

2. The device of claim 1, wherein the needle comprises a closed shank and the sharp end is open.

3. The device of claim 1, wherein the housing independently selectively engages the needle and stylet.

4. The device of claim 1, wherein the housing disengages the needle while simultaneously engaging the stylet.

5. The device of claim 1, wherein the housing selectively engages and disengages the needle in response to relative rotation between the needle and the housing.

6. The device of claim 1, wherein the housing selectively engages and disengages the stylet in response to relative rotation between the stylet and the housing or between the needle and the housing.

7. The device of claim 1, wherein relative rotation between the needle and the housing selectively disengages the needle from the housing, and the relative rotation that disengages the needle also engages the stylet to the housing.

8. The device of claim 1, wherein the housing, the needle and the stylet have cooperating members that interact to selectively fix the needle and stylet against axial movement.

9. The device of claim 7, wherein the cooperating members comprise a groove and a projection which slides into the groove.

10. The device of claim 9, wherein the groove comprises a separate needle groove and a stylet groove, and the stylet groove is angled to advance the stylet in response to relative rotation between the stylet and the housing.

11. The device of claim 10, wherein the needle groove is contained in a plane perpendicular to a direction of axial movement of the needle in the housing.

12. The device of claim 10, wherein the stylet groove comprises a plurality of substantially parallel, non-communicating grooves.

13. The device of claim 9, wherein the projection comprises a projection from the needle that rotates into engagement with the groove to selectively fix the needle against axial movement relative to the housing.

14. The device of claim 13, wherein the groove comprises a thread in a wall of the housing.

15. The device of claim 13, wherein the groove comprises a gap in a collar that limits axial movement of the needle relative to the housing except when the projection from the needle aligns with the gap.

16. The device of claim 8, wherein the cooperating members comprise triggers on each of the stylet and needle which are independently actuated to move the stylet or needle relative to the housing.

17. The device of claim 16, wherein the triggers comprise deformable members on each of the stylet and needle, wherein the deformable members in a first position engage the housing, but wherein each of the deformable members are selectively deformable out of engagement with the housing to move the deformable member and the stylet or needle to which the deformable member is attached.

18. The device of claim 1, further comprising a spacer extending from a distal end of the instrument.

19. The device of claim 18, wherein a length of the spacer may be selectively altered.

20. The device of claim 1, further comprising a stop member comprising a stop portion that opposes advancement of the needle along the path of insertion beyond a preselected distance.

21. The device of claim 20, wherein the stop portion comprises an aperture or notch of a size that permits the needle to pass through it, but which abuts against an enlarged diameter portion of the device to oppose advancement of the needle beyond the preselected distance.

22. The device of claim 21, wherein the needle further comprises a first mating member, and the aperture or notch comprises a second mating member, wherein the first and second mating members cooperate to resist rotation and withdrawal of the needle.

23. The device of claim 22, wherein the first and second mating members are engaged by rotating the needle.

24. The device of claim 21, wherein the stop member comprises a plate.

25. The device of claim 24, wherein the plate includes a series of slots with notches at pre-selected positions in which the needle can seat.

26. The device of claim 20, wherein the stop member comprises a movable member that is selectively alignable with the path of insertion of the needle.

27. The device of claim 26, wherein the stop member is pivotable into and away from the path of insertion of the needle.

28. The device of claim 27, wherein the stop member is a pivotable arm comprising a plurality of notches that are selectively alignable with a template position.

29. The device of claim 28, wherein the pivotable arm pivots in a plane substantially perpendicular to the path of insertion.

30. The device of claim 20, wherein the stop member further includes an ultrasound transducer attachment bracket.

31. The device of claim 20, wherein the stop member comprises a proximal stop member and distal stop member that are movable apart from one another along the path of insertion of the needle to a limit distance, and the proximal and distal stop members define aligned apertures or notches through which the needle may be inserted, and the apertures or notches of the distal stop member are smaller than the apertures of the proximal stop member, so that advancement of the needle along the path of insertion moves the distal stop member away from the proximal stop member, but the apertures or notches of the distal stop member are deformable to allow the needle to be inserted therethrough by the application of sufficient insertion force after the distal stop member reaches the limit distance.

32. A brachytherapy device, comprising:
an elongated needle having a sharp end for insertion into target tissue;
an elongated stylet which can slide through the needle; and
a housing that selectively engages the needle and stylet to selectively fix the needle and stylet against axial movement, wherein relative rotation between the housing and needle selectively engages the needle to the housing to fix the needle against axial movement relative to the housing, and relative rotation between the housing and the stylet selectively engages the stylet to the housing to fix the stylet against axial movement relative to the housing.

33. The device of claim 32, wherein relative rotation between the housing and the needle selectively disengages the needle from the housing to permit axial movement of the needle relative to the housing, and relative rotation between the housing and the stylet selectively disengages the stylet from the housing to permit axial movement of the stylet relative to the housing.

34. The device of claim 33, wherein the same relative rotation between the housing and the needle that selectively engages the needle to the housing also disengages the stylet from the housing.

35. The device of claim 34, wherein the housing, the needle and the stylet have cooperating members that interact to selectively fix the needle and stylet against axial movement.

36. The device of claim 35, wherein the cooperating members comprise a groove and a projection which slides into the groove.

37. The device of claim 36, wherein the groove comprises a separate needle groove and a stylet groove, and the stylet groove is angled to advance the stylet in response to relative rotation between the stylet and the housing.

38. The device of claim 37, wherein the needle groove is contained in a plane perpendicular to a direction of axial movement of the needle in the housing.

39. The device of claim 37, wherein the stylet groove comprises a plurality of substantially parallel, non-communicating grooves.

40. The device of claim 36, wherein the projection comprises a projection from the needle that rotates into engagement with the groove to selectively fix the needle against axial movement relative to the housing.

41. The device of claim 40, wherein the groove comprises a thread in a wall of the housing.

42. The device of claim 40, wherein the groove comprises a gap in a collar that limits axial movement of the needle relative to the housing except when the projection from the needle aligns with the gap.

43. A brachytherapy device, comprising:
an elongated needle having a sharp end for insertion into target tissue;
an elongated stylet which can slide through the needle; and
a housing that selectively engages the needle to selectively fix the needle against axial movement, wherein rotation of the needle relative to the housing selectively engages the needle to the housing to fix the needle against axial movement relative to the housing, whereby rotation of the needle also reduces frictional engagement between the needle and the target tissue.

44. The device of claim 43, wherein the housing and the needle have cooperating members that interact to selectively fix the needle and stylet against axial movement.

45. The device of claim 44, wherein the cooperating members comprise a needle groove and a projection which slides into the groove.

46. The device of claim 45, wherein the needle groove is contained in a plane perpendicular to a direction of axial movement of the needle in the housing.

47. The device of claim 46, wherein the projection comprises a projection from the needle that rotates into engagement with the needle groove to selectively fix the needle against axial movement relative to the housing, and the groove comprises a thread in a wall of the housing.

48. The device of claim 45, wherein the groove comprises a gap in a collar that limits axial movement of the needle relative to the housing except when the projection from the needle aligns with the gap.

49. An instrument for use in implanting seeds within a patient's body, comprising:
a hollow needle coincident with a central axis of the instrument, the needle having a needle tip that defines a distal end of the instrument, a needle shaft extending from the needle tip and a needle extension portion attached to a proximal end of the needle shaft;
a stylet insertible into the needle shaft from the proximal end of the needle, the stylet having a distal end, a stylet shaft extending from the distal end and a stylet hub attached to a proximal end of the stylet;

a housing that extends at least partially around the central axis and has a distal end through which the needle shaft extends, the housing being shaped to receive and engage the needle extension portion and the stylet hub to coordinate axial movement of the needle and stylet relative to each other and the housing.

50. The instrument of claim 49, wherein the housing is channel-shaped and has a generally arcuate cross-section, and an inner surface of the housing is formed with a series of spaced threads.

51. The instrument of claim 49, wherein the housing is generally tubular with an axial slot formed therein.

52. The instrument of claim 51, wherein the housing is hinged in the axial direction such that it can be opened to receive the needle and stylet and closed for operation.

53. The instrument of claim 49, wherein the distal end of the housing has an opening sized larger than the needle shaft and smaller than a cross-section of the needle extension portion, thereby allowing axial movement of the needle relative to the housing over a predetermined distance but preventing the needle extension portion from advancing beyond the distal end of the housing.

54. The instrument of claim 49, wherein a proximal end of the housing has an opening sized larger than the needle extension portion such that the needle can be inserted into and retracted from the proximal end of the housing in the axial direction.

55. The instrument of claim 49, wherein the housing is channel-shaped and has a generally arcuate cross-section, and an inner surface of the housing is formed with a series of spaced, interrupted threads extending from a proximal end of the housing towards the distal end, the housing having respective collars formed at the distal and proximal ends, wherein the distal collar defines a first opening transverse to the central axis and sized larger than the needle shaft and smaller than the needle extension portion, the first collar thereby preventing the needle extension portion from being advanced in the axial direction beyond the distal end of the housing, and wherein the proximal collar defines a second opening transverse to the central axis and sized larger than the needle extension portion thereby allowing the needle to be retracted in the axial direction and removed from the housing.

56. The instrument of claim 55, wherein the first and second openings communicate with respective first and second gaps in the distal and proximal collars, the first and second gaps being defined between respective terminal ends of the distal and proximal collar members and a common side of the housing, and wherein the first and second gaps are aligned in an axial direction.

57. The instrument of claim 49, wherein the housing includes a needle receiving feature and the needle includes a needle engaging feature engageable with the needle receiving feature, wherein when the needle is engaged with the housing, the needle cannot be moved in the axial direction relative to the housing.

58. The instrument of claim 57, wherein the needle receiving feature is a groove formed in an inner surface of the housing and extending in a direction transverse to the axial direction, and wherein the needle engaging feature is a projection from an outer surface of the needle extension portion, the projection being engageable with the groove when the needle is rotated relative to the housing.

59. The instrument of claim 49, wherein the needle extension portion is rotatably engageable with the housing such that over a first part of a rotation between the needle extension portion and the housing prevents axial movement of the needle and over a second portion of the rotation the needle extension portion can be retracted in the axial direction relative to the housing.

60. The instrument of claim 1, wherein the housing is generally tubular and has an axial slot formed therein extending from a proximal end to a point spaced from the distal end, the slot having a first side edge formed with a first repeating pattern of projection and a second side edge formed with a second pattern of projections, wherein the needle extension portion is a knob having a hub portion slidable within the housing, and the stylet hub is a knob having a hub portion slidable within the housing, the knobs extending through the slot and being depressible in a radial direction, the needle knob having an engagement portion for engaging the first repeating pattern and the stylet knob having a engagement portion for engaging the second repeating pattern, and wherein each of the needle and the stylet is selectively engageable with the respective side of the slot to prevent axial movement relative to housing.

61. The instrument of claim 49, wherein the needle extension portion includes an axial groove formed therein parallel to the central axis and aligned with the needle shaft, the groove being sized to receive seeds to be loaded into the needle shaft and the stylet shaft.

62. The instrument of claim 49, further comprising a pusher used to cover seeds in the needle extension portion prior to loading and to load seeds into the needle shaft, wherein the needle extension portion is formed with an axial slot extending from a proximal end of the needle extension portion to the proximal end of the needle shaft, the axial slot being sized to receive the pusher and having a groove sized to receive seeds formed in a base thereof.

63. The instrument of claim 49, wherein the needle extension portion is formed with an axial slot extending from a proximal end of the needle extension portion to the proximal end of the needle shaft, the axial slot having a groove sized to receive seeds formed in a base thereof, and wherein the stylet hub is shaped to slide within the slot with the stylet shaft in the groove.

64. The instrument of 63, wherein the housing is channel-shaped and has a generally arcuate cross-section, and an inner surface of the housing is formed with a series of spaced, interrupted threads extending from a proximal end of the housing towards the distal end, the housing having respective first and second collars formed at the distal and proximal ends, wherein the first collar defines a first opening transverse to the central axis and sized larger than the needle shaft and smaller than the needle extension portion, the first collar thereby preventing the needle extension portion from being advanced in the axial direction beyond the distal end of the housing, wherein the second collar defines a second opening transverse to the central axis and sized larger than the needle extension portion thereby allowing the needle to be retracted in the axial direction and removed from the housing, and wherein the stylet hub has a projection extending in a radial direction relative to the central axis and rotatable into engageable with one of the threads of the housing such that further rotation causes the stylet to advance in the axial direction relative to the needle and the housing.

65. The instrument of claim 49, further comprising a spacer attached to a distal end of the housing.

66. The instrument of claim 65, wherein the spacer is resilient such that with the spacer in contact with a stationary object, the spacer flexes to permit the housing to be advanced slightly in the axial direction under a force and returned to a normal position when the force is relaxed.

67. The instrument of claim 66, wherein the spacer is an arm selectively engageable with the body to position a distal end of the arm at a predetermined axial distance from the distal end of the housing.

68. The instrument of claim 67, wherein the arm is selectively slidable along a side of the housing.

69. The instrument of claim 65, wherein the spacer is a pair of resilient wings attached to the distal end of the housing on opposite sides of the needle shaft.

70. The instrument of claim 49, wherein the housing is channel-shaped and has a generally arcuate cross-section, the housing having first and second collars respectively formed at distal and proximal ends thereof,
wherein the first collar defines a first opening transverse to the central axis and sized larger than the needle shaft and smaller than the needle extension portion, the first collar thereby preventing the needle extension portion from being advanced in the axial direction beyond the distal end of the housing,
wherein the second collar defines a second opening transverse to the central axis and sized larger than the needle extension portion, the second opening communicating with a gap defined between a terminal end of the collar and a side of the housing, and
wherein the needle extension portion is rotatable within the housing and has a generally cylindrical outer surface with an axial rib formed thereon, the rib preventing the needle from being retracted relative to the housing unless the rib is aligned with the gap in the second collar.

71. The instrument of claim 49 wherein the distal end of the housing includes a flat portion designed to contact a stationary object to maintain the instrument at a predetermined axial position with the needle tip inserted in the body to a predetermined insertion depth.

72. The instrument of claim 71, wherein the housing includes a step formed in its outer surface spaced proximally from the flat portion, and wherein the step can be brought into contact with the stationary object to maintain the instrument at a predetermined axial position with the needle inserted in the body to an over-insertion depth.

73. The instrument of claim 71, wherein the housing includes a groove formed in its outer surface spaced proximally from the flat portion, the stationary object includes a rib sized to fit within the groove, and the groove can be engaged with the rib on the stationary object to maintain the instrument at a predetermined axial position with the needle inserted in the body to an over-insertion depth.

74. The instrument of claim 49, wherein the stylet hub is includes a coupling that selectively couples with the needle extension portion when the stylet hub is moved within a predetermined distance of the needle extension portion.

75. The instrument of claim 74, wherein the coupling includes a hook extending in a distal direction from the stylet hub, and the needle extension portion has a hook receiver positioned near its distal end, and wherein when the stylet is advanced in the axial direction toward the distal end of the needle extension portion, the hook on the stylet hub engages the hook receiver on the needle extension portion.

76. A needle stop for use in a brachytherapy procedure to prevent a needle extending in an axial direction from advancing beyond a predetermined position, the needle stop comprising a body extending transverse to the axial direction and having:
a needle receiving side with a plurality of slots formed therein in a direction perpendicular to the axial direction, each of the slots being sized to allow a shaft of a needle to pass therethrough as the needle is inserted;
a needle stop surface on the needle receiving side that stops insertion of the needle through contact by an enlarged portion of the needle with the stop surface; and
an attachment portion that allows the needle stop to be attached to an object.

77. A needle guide through which a brachytherapy needle having a needle tip can be inserted, the needle guide comprising:
a stationary first member having a first plurality of apertures extending in an axial direction and sized to allow the needle shaft to pass therethrough; and
a second member that is coupled to the first member for movement in a direction of needle insertion, the second member having a second plurality of apertures corresponding to the first plurality of apertures, the second plurality of apertures being dimensioned smaller than the needle shaft;
whereby the second member receives a tip of a needle inserted through the first member from the insertion side and into one of the second plurality of apertures, the second member moving with and guiding the tip as the needle advances in the axial direction.

78. A needle stop for use in a brachytherapy procedure with a needle being inserted in an insertion direction, the needle having a needle tip, a needle shaft extending from the needle tip and a needle extension portion having a cross-section greater than a cross-section of the needle shaft, the needle stop comprising:
a stationary base; and
a movable stop arm pivotably attached to the based and positionable transverse to the insertion direction at a predetermined location, the stop arm having an edge against which the needle extension portion is brought in contact to prevent the needle from being advanced in the insertion direction.

79. The needle stop of claim 78, wherein the arm includes at least one groove through which the needle shaft passes as the needle is advanced in the insertion direction.

80. The needle stop of claim 25, wherein the arm includes a locking rib engageable with a corresponding groove formed in the needle to stabilize the needle.

81. A method of implanting brachytherapy seeds, the method comprising:
providing an elongated needle having a sharp end for insertion into target tissue, an elongated stylet which can slide through the needle, and a housing that selectively engages the needle to selectively fix the needle against axial movement by rotating the needle;
rotating the needle to engage the needle with the housing;
inserting brachytherapy seeds into the needle;
inserting the stylet into the needle to advance the seeds toward a sharp end of the needle;

inserting the needle into the target tissue;

rotating the needle to disengage the needle from the housing and permit axial movement of the needle; and withdrawing the needle over the stylet to implant the seeds in the target tissue.

82. The method of claim 81, wherein the housing further selectively engages the stylet to selectively fix the stylet against axial movement when the stylet is rotated into engagement with the housing, and the stylet is rotated to engage the stylet with the housing prior to withdrawing the needle.

83. The method of claim 82, wherein rotating the stylet also axially advances the stylet.

84. The method of claim 83, wherein rotating the stylet to engage the housing and axially advance the stylet also rotates the needle to disengage it from the housing.

85. A method of performing a brachytherapy treatment using an instrument, the instrument comprising:

a hollow needle having a needle tip that defines a distal end of the instrument, a needle shaft that defines a central axis of the instrument and a needle extension portion joined to the proximal end of the needle shaft, the needle shaft containing seeds to be implanted within a patient's body;

a stylet inserted through the needle extension portion and into the needle shaft, the stylet having a distal end in contact with a most proximal seed and a proximal end with a stylet hub adjacent the needle extension portion;

a housing extending partially around the central axis and within which the needle extension portion and the stylet hub are rotatably coupled, the housing having a distal end through which the needle shaft extends and a proximal end through which the needle extension portion extends;

the method comprising:

advancing the instrument in an axial direction to insert the needle into the body;

engaging the stylet with the housing to cause the stylet to advance in the axial direction relative to the needle by a predetermined distance to implant the most distal seed;

disengaging the needle from the housing; and retracting the needle in the axial direction relative to the stylet and the housing, which remain stationary, to implant remaining seeds.

86. The method of claim 85, wherein advancing the instrument comprises advancing the instrument in the axial direction into contact with a stop that is positioned at a predetermined location to prevent further axial movement of the instrument.

87. The method of claim 85, wherein advancing the instrument comprises advancing the instrument in an axial direction to insert the needle tip to a predetermined over-insertion depth, retracting the instrument in the axial direction, and advancing the instrument to insert the needle tip to an insertion depth less than the over-insertion depth.

88. The method of claim 87, wherein advancing the instrument comprises advancing the instrument such that the housing contacts a stop positioned at a predetermined location with the distal end of the housing advanced beyond the stop to position the needle tip to a predetermined over-insertion depth, retracting the instrument in the axial direction and re-advancing the instrument such that the distal end of the housing contacts the stop to position the needle at the insertion depth.

89. The method of claim 85, wherein engaging the stylet with the housing comprises rotating the stylet relative to the housing, and wherein the stylet advances in the axial direction during the rotation.

90. The method of claim 89, wherein rotating the stylet rotates the needle relative to the housing.

91. The method of claim 85, wherein engaging the stylet with the housing comprises rotating the needle extension portion relative to the housing, which in turn rotates that stylet relative to the housing and causes the stylet to advance in the axial direction.

* * * * *